US012731250B2

(12) United States Patent
Kim et al.

(10) Patent No.: US 12,731,250 B2
(45) Date of Patent: Sep. 8, 2026

(54) SYNTHESIS SINGLEPLEX FROM MULTIPLEX BRIGHTFIELD IMAGING USING GENERATIVE ADVERSARIAL NETWORK

(71) Applicant: Ventana Medical Systems, Inc., Tuscon, AZ (US)

(72) Inventors: Jungwon Kim, Los Angeles, CA (US); Auranuch Lorsakul, Santa Clara, CA (US); Yao Nie, Sunnyvale, CA (US); Xingwei Wang, Sunnyvale, CA (US); Zuo Zhao, Palo Alto, CA (US)

(73) Assignee: Ventana Medical Systems, Inc., Tucson, AZ (US)

( * ) Notice: Subject to any disclaimer, the term of this patent is extended or adjusted under 35 U.S.C. 154(b) by 613 days.

(21) Appl. No.: 18/064,844

(22) Filed: Dec. 12, 2022

(65) Prior Publication Data

US 2023/0186470 A1 Jun. 15, 2023

Related U.S. Application Data

(60) Provisional application No. 63/289,867, filed on Dec. 15, 2021.

(51) Int. Cl.
*G06K 9/00* (2022.01)
*G01N 33/53* (2006.01)
(Continued)

(52) U.S. Cl.
CPC ........... *G06T 7/0012* (2013.01); *G01N 33/53* (2013.01); *G06V 10/70* (2022.01); *G06T 2207/30024* (2013.01)

(58) Field of Classification Search
None
See application file for complete search history.

(56) References Cited

U.S. PATENT DOCUMENTS

2016/0358335 A1 12/2016 Chukka et al.
2020/0258223 A1* 8/2020 Yip ......................... G06F 18/21
2021/0325308 A1* 10/2021 Kannan .............. G01N 21/6458

FOREIGN PATENT DOCUMENTS

AU 2015261891 A1 * 10/2016 ........... G06T 7/0012
WO 2020139442 A2 7/2020
WO 2021124293 A1 6/2021

OTHER PUBLICATIONS

Zhuge (Deep learning 2D and 3D optical sectioning microscopy using cross-modality Pix2Pix cGAN image translation. vol. 12, No. 12 / Dec. 1, 2021 / Biomedical Optics Express 7526-7543, published Nov. 12, 2021). (Year: 2021).*

(Continued)

*Primary Examiner* — Wei Wen Yang
(74) *Attorney, Agent, or Firm* — Mughal Gaudry & Franklin PC

(57) ABSTRACT

A multiplex image is accessed that depicts a particular slice of a particular sample stained with two or more dyes. Using a Generator network, a predicted singleplex image is generated that depicts the particular slice of the particular sample stained with each of the expressing biomarkers. The Generator network may have been trained by training a machine-learning model using a set of training multiplex images and a set of training singleplex images. Each of the set of training multiplex images depicted a slice of a sample stained with two or more dyes. Each of the set of training singleplex images depicted a slice of a sample stained with a single dye. The machine-learning model included a Discriminator network configured to discriminate whether a given image was generated by the Generator network or was a singleplex image of a real slide. The method further includes outputs the predicted singleplex image.

21 Claims, 22 Drawing Sheets
(20 of 22 Drawing Sheet(s) Filed in Color)

(51) Int. Cl.
*G06T 7/00* (2017.01)
*G06V 10/70* (2022.01)

(56) References Cited

OTHER PUBLICATIONS

Ruifrok, et al., "Quantification of Histochemical Staining by Color Deconvolution" Analyt Quant Cytol Histol 2001;23:291-299.
Miao, et al., "Endmember Extraction from Highly Mixed Data Using Minimum Volume Constrained Nonnegative Matrix Factorization," in IEEE Transactions on Geoscience and Remote Sensing, vol. 45, No. 3, pp. 765-777, Mar. 2007, doi: 10.1109/TGRS.2006.888466.
Isola, et al., "Image-to-Image Translation with Conditional Adversarial Networks", CVPR, 2017, arXiv:1611.07004v3, 17 pages.
Zhu, et al., "Unpaired Image-to-Image Translation Using Cycle-Consistent Adversarial Networks", in IEEE International Conference on Computer Vision (ICCV), 2017, 18 pages.
Wang, et al., "High-Resolution Image Synthesis and Semantic Manipulation with Conditional GANs", in CVPR, 2018, arXiv:1711.11585v2, 14 pages.
Zhu, et al., "Toward Multimodal Image-to-Image Translation", in NIPS, 2017, arXiv:1711.11586v4, 12 pages.
Ghahremani et al., "Deep Learning-Inferred Multiplex ImmunoFluorescence for IHC Image Quantification", bioRxiv, 2021, 23 pages.
Application No. PCT/US2022/081378 , International Search Report and the Written Opinion, Mailed on Feb. 27, 2023, 11 pages.
Xu et al., "GAN-based Virtual Re-Staining: A Promising Solution for Whole Slide Image Analysis", Available Online at: https://arxiv.org/pdf/1901.04059.pdf, Jan. 13, 2019, 16 pages.
English Translation of Notice of Reasons for Rejection for Japanese Patent Application No. 2024-535863, dated Jul. 1, 2025.
Zhaoyang Xu et al., "GAN-based Virtual Re-Staining: A Promising Solution for Whole Slide Image Analysis", Internet Archive, Jan. 13, 2019, pp. 1-16, retrieved on Jun. 20, 2025 from arxiv.org/pdf/1901.04059v1.
Notice of Reasons for Rejection for Japanese Patent Application No. 2024-535862, dated Jan. 6, 2026.

* cited by examiner

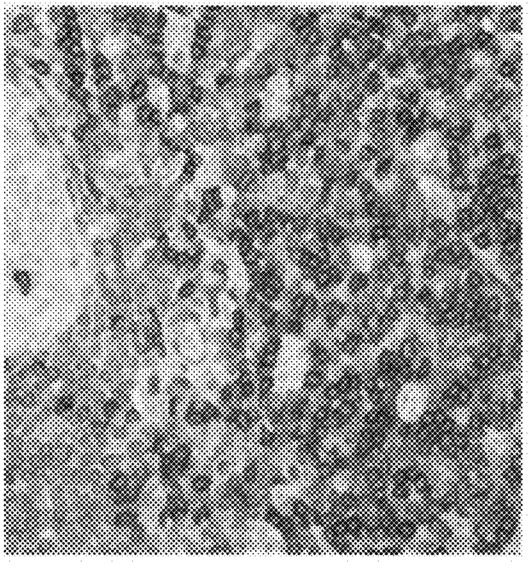
FIG. 1F
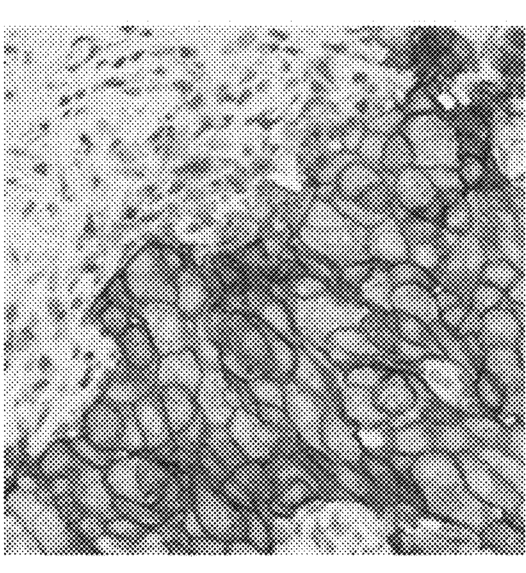
FIG. 1E
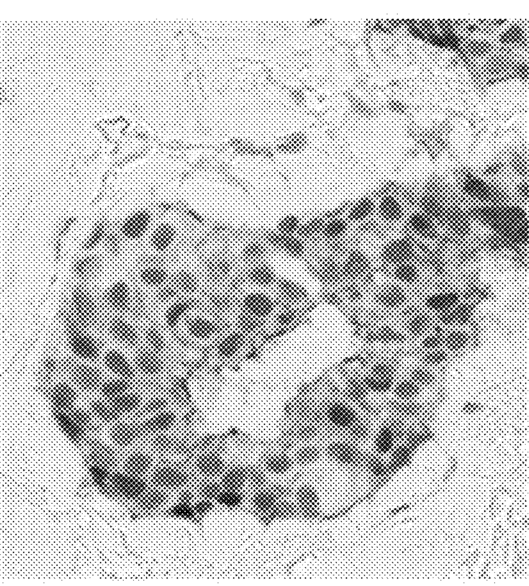
FIG. 1D

| Methods | Pros | Cons |
|---|---|---|
| Option I: Color unmixing and remixing | • Perfect tissue **matching**<br>• No **registration** required | • Dependent on pure **reference** colors<br>• **Dependent** on staining protocols, tissue, scanners, sites |
| Option II: Adjacent staining singleplex | • **True** staining intensity levels | • Not good **tissue** matches<br>• **Dependent** on staining protocols, tissue, scanners, sites |

FIG. 2

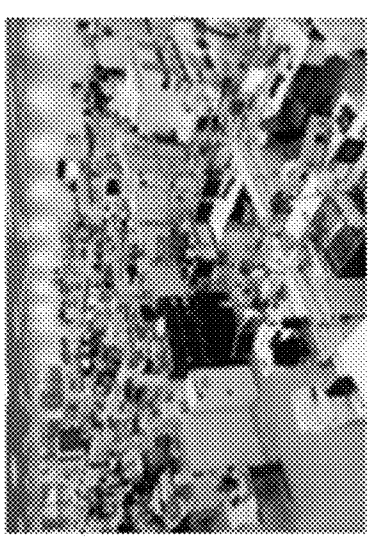
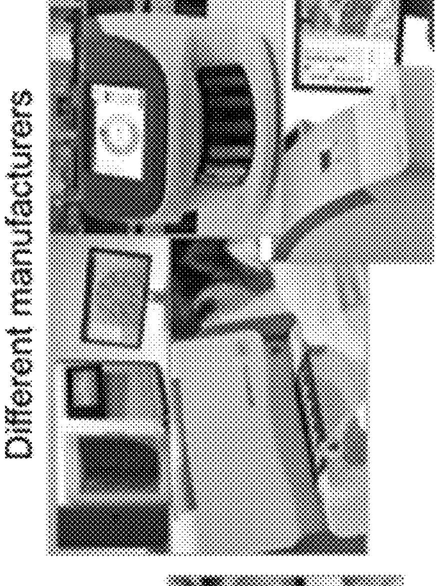
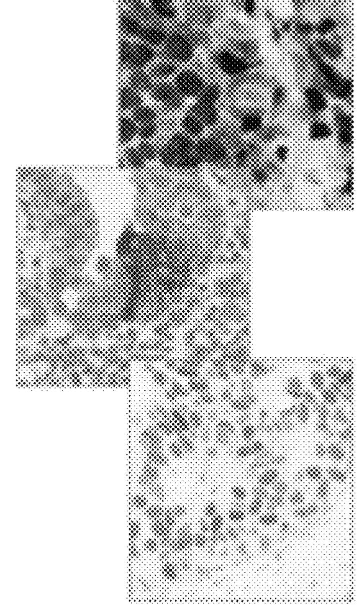
FIG. 3

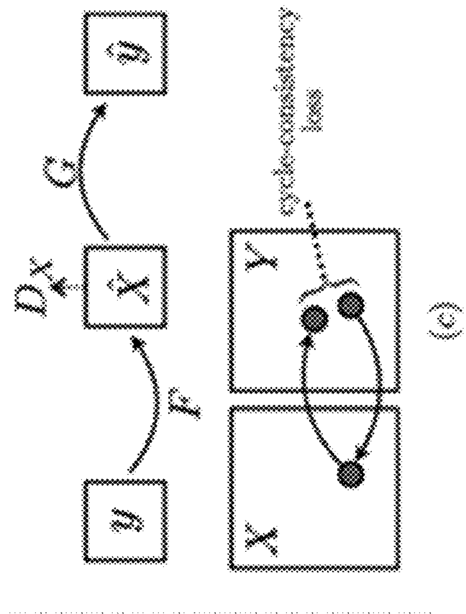
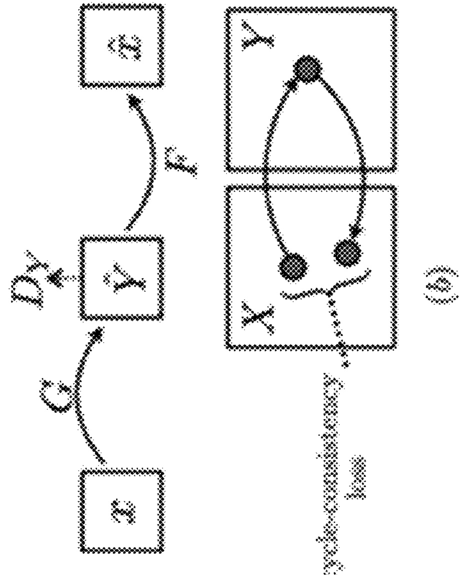
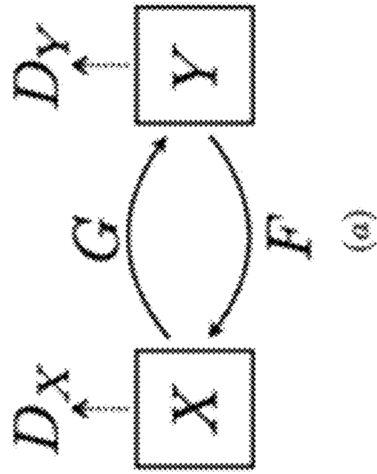
FIG. 5

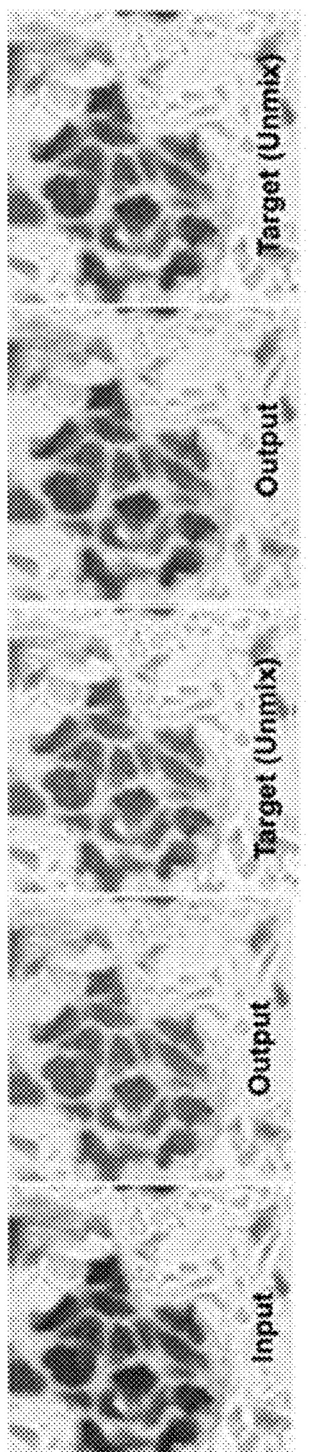
ER/PR, DP200, same slide, different regions, breast
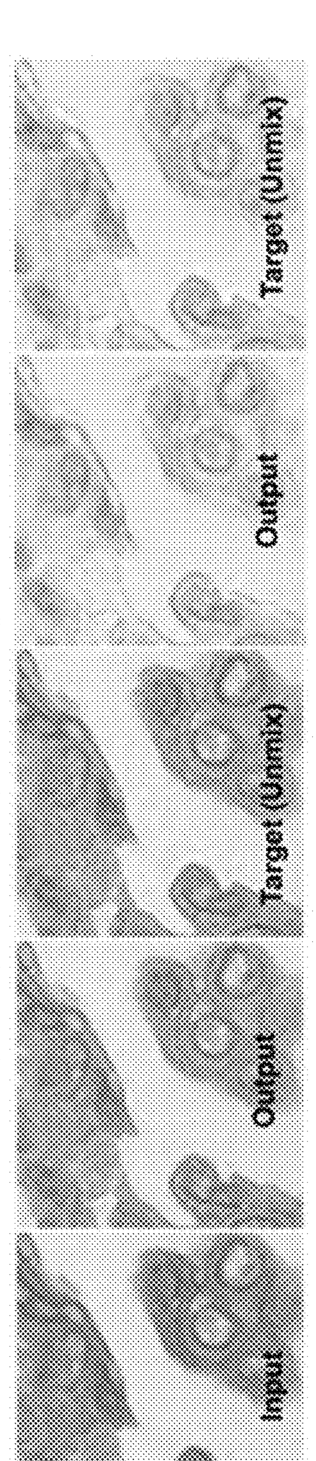
PDL1/PanCK, DP200, same slide, different regions, NSCL
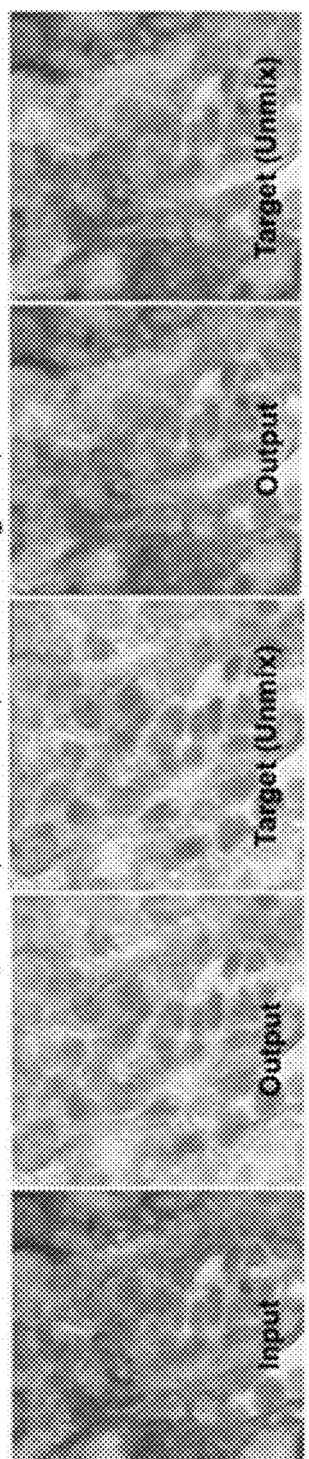
PDL1/PanCK, DP200, different slide, different patients, NSCL
FIG. 8

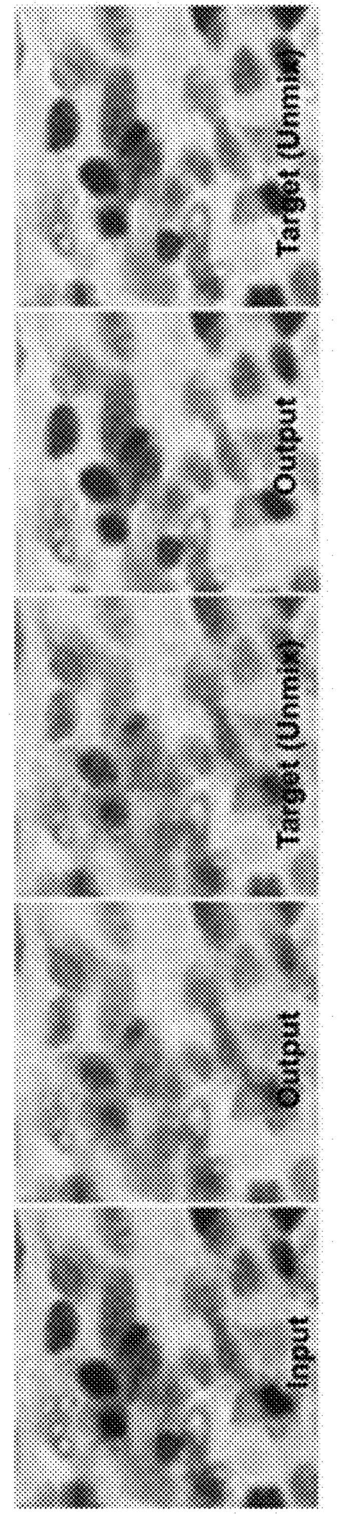
Ki67/CD8, iScanHT, different patients, different slides, multiple indications
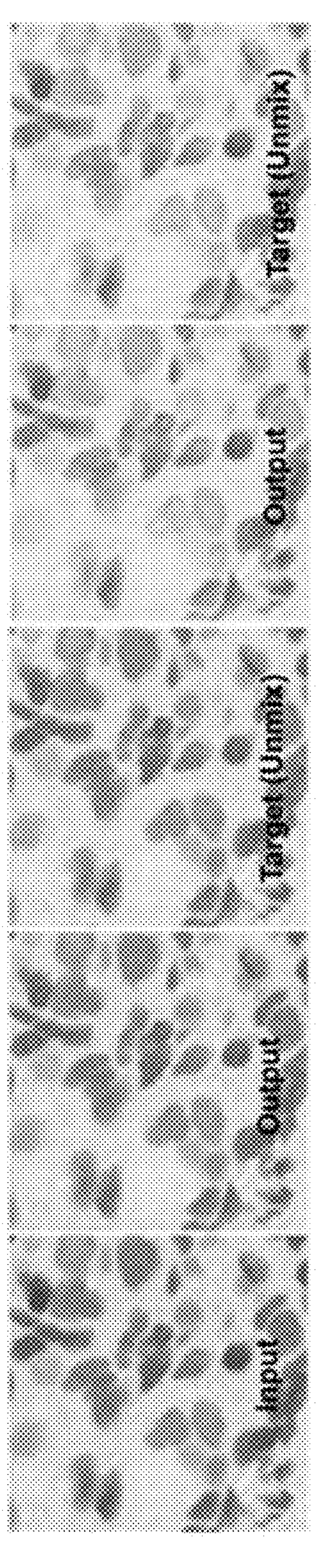
ER/PR, DP200, same slide, different regions, breast
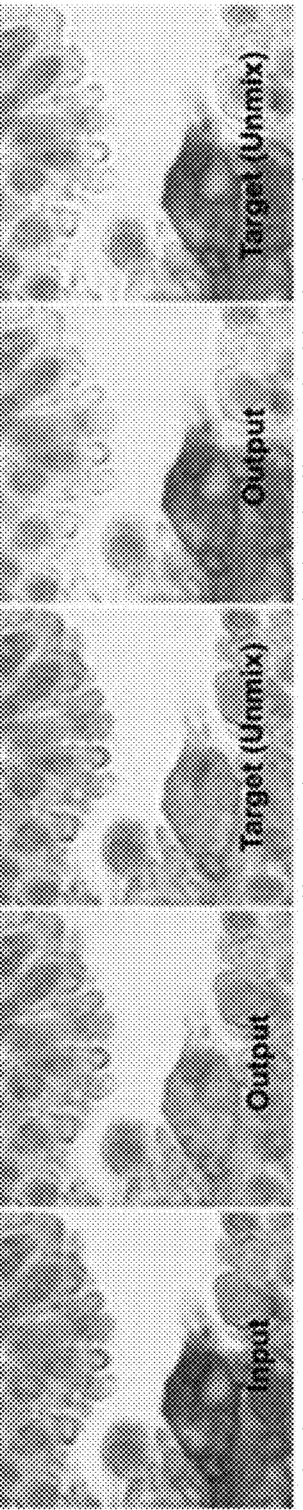
PDL1/PanCK, DP200, different slide, different patients, NSCL
FIG.9

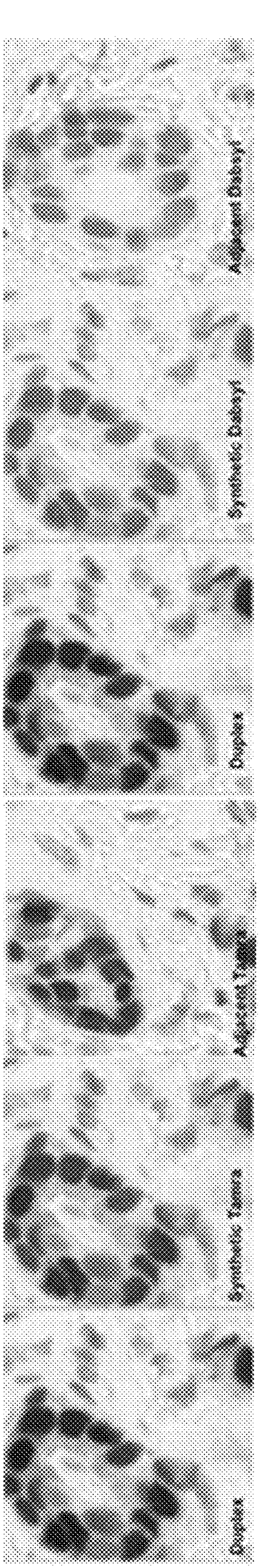
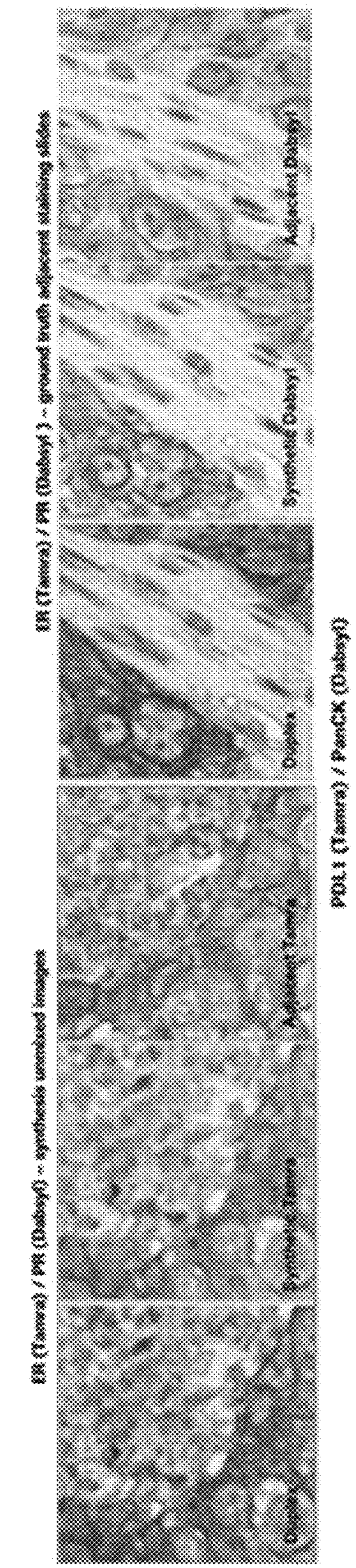
FIG. 10

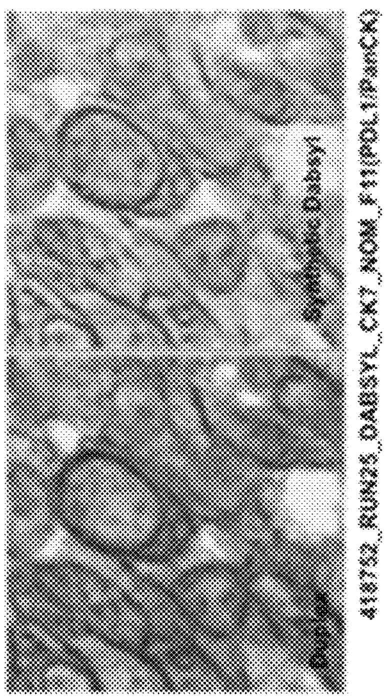
FIG. 11
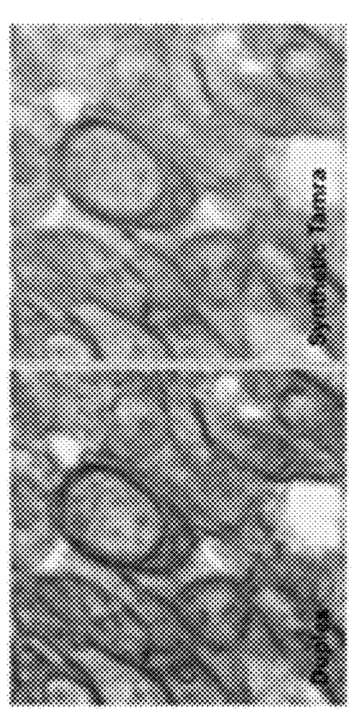

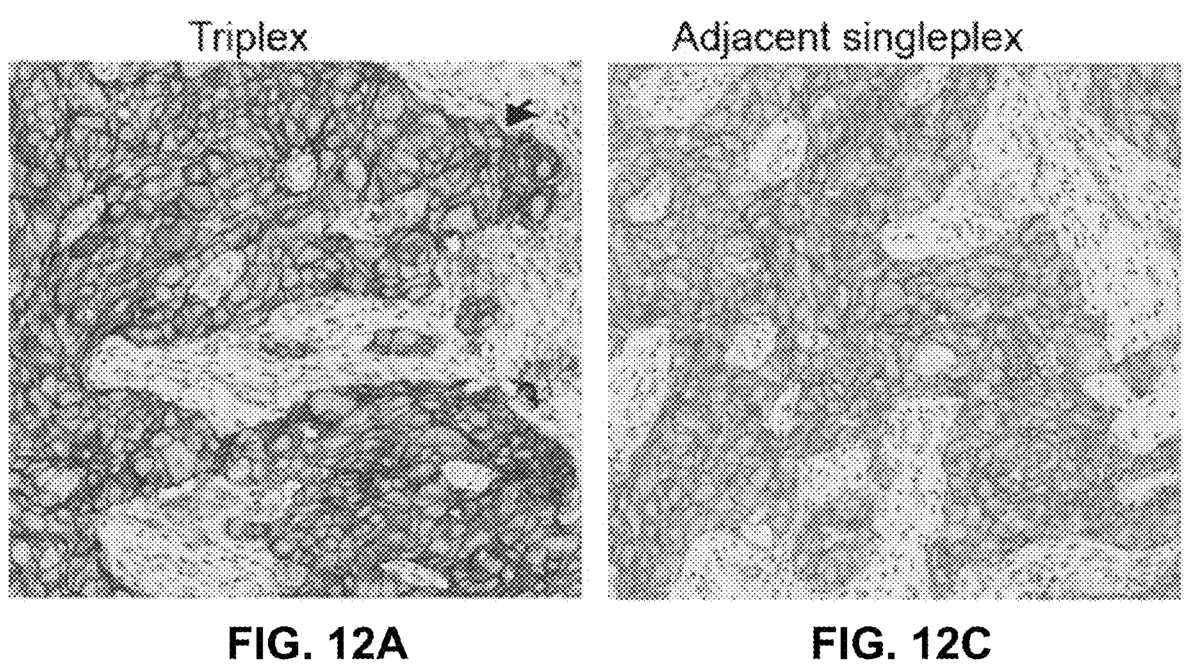
FIG. 12A
FIG. 12C
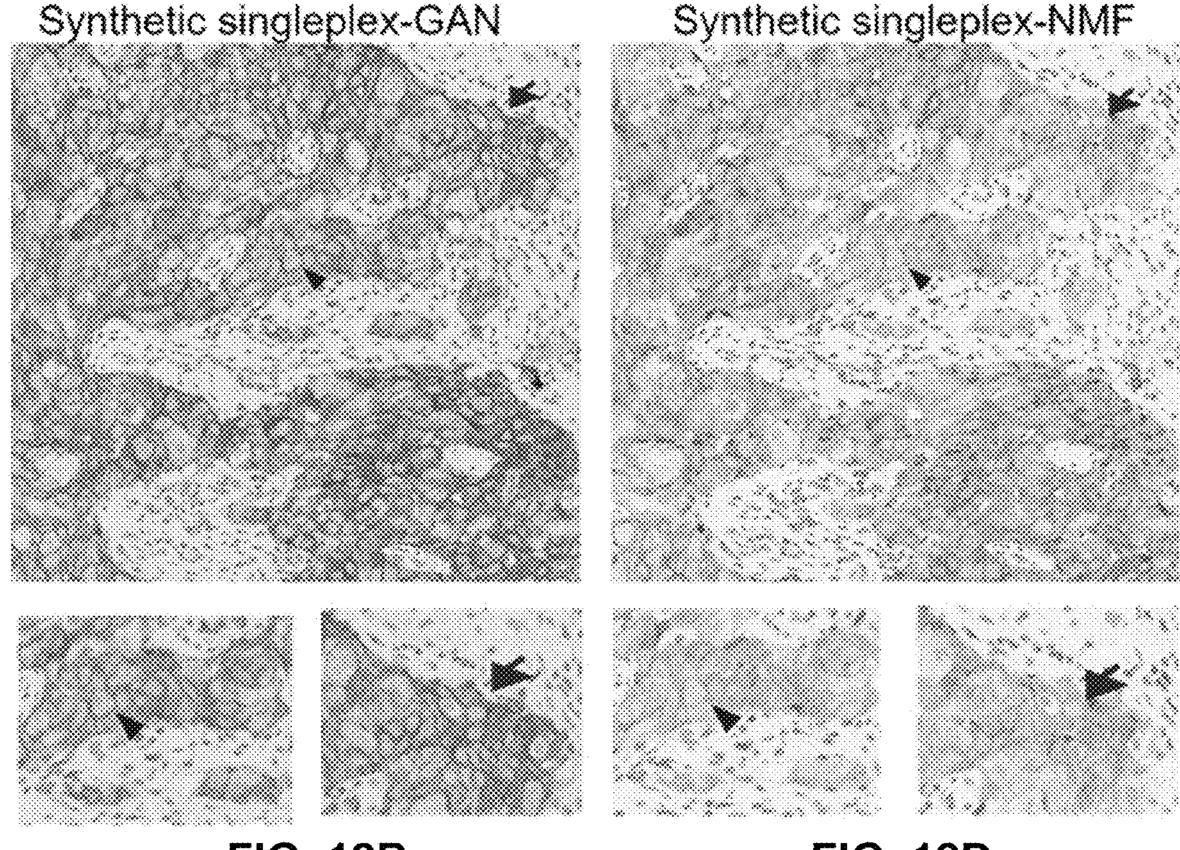
FIG. 12B
FIG. 12D

FIG. 16A
FIG. 16C
FIG. 16B
FIG. 16D

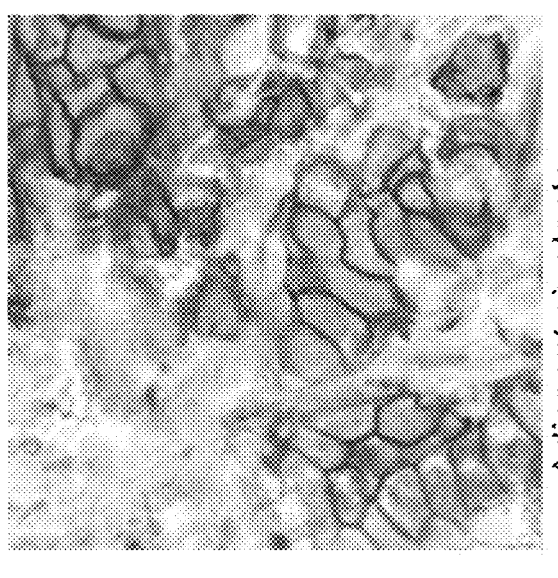
Adjacent singleplex
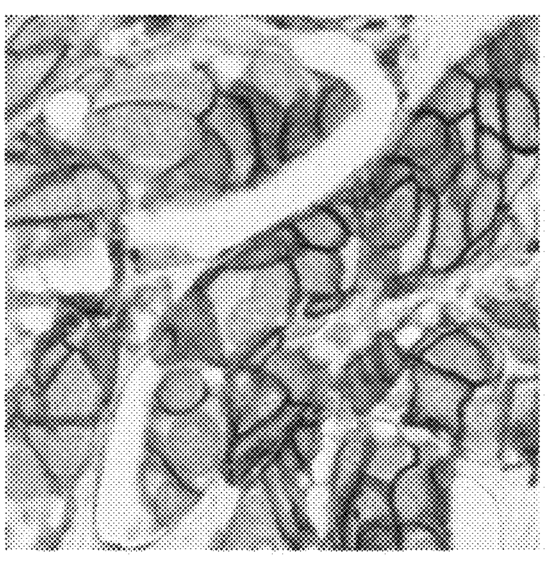
GAN Synthetic Results
FIG. 20
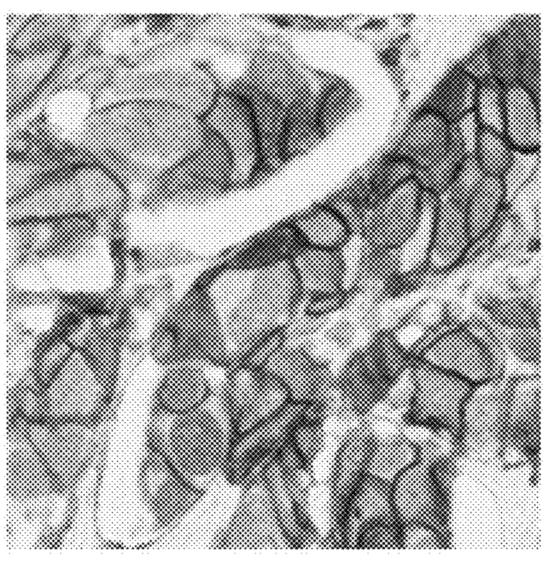
Triplex

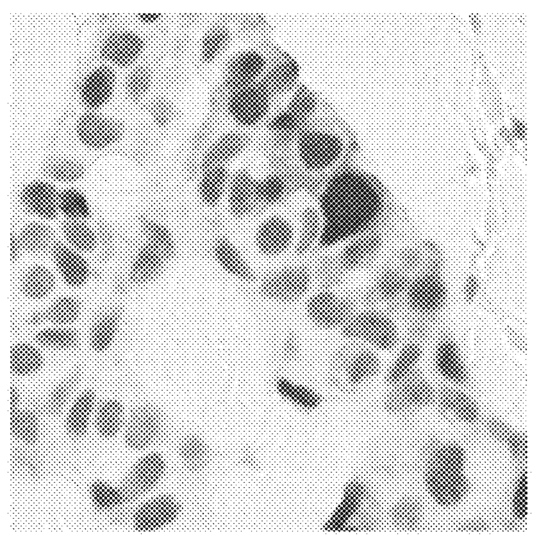
Adjacent singleplex
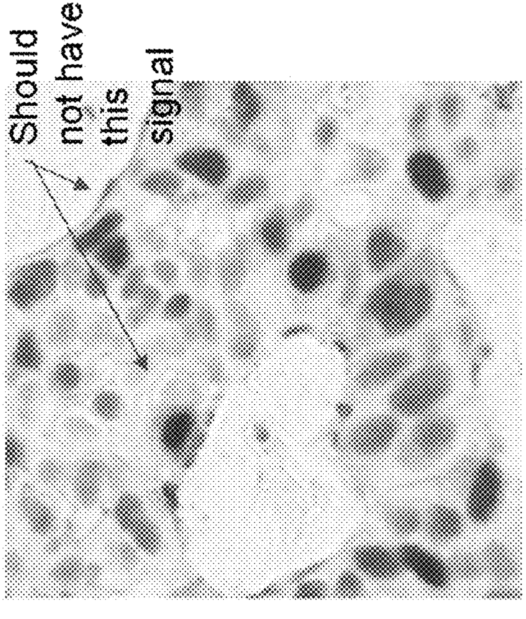
GAN Synthetic Results
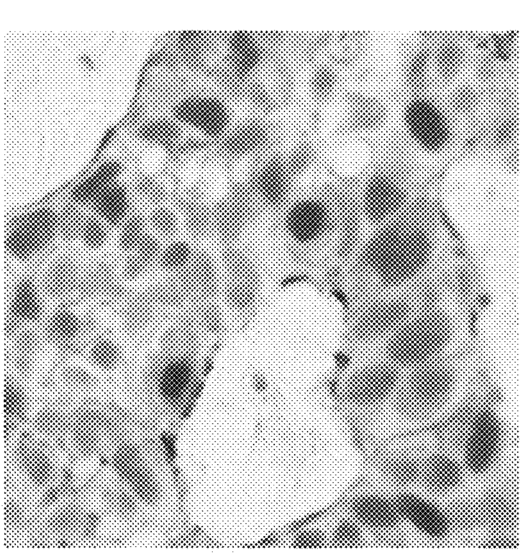
Triplex
FIG. 21

SYNTHESIS SINGLEPLEX FROM MULTIPLEX BRIGHTFIELD IMAGING USING GENERATIVE ADVERSARIAL NETWORK

CROSS-REFERENCE TO RELATED APPLICATIONS

This application claims the benefit of and the priority to U.S. Provisional Application No. 63/289,867, filed on Dec. 15, 2021, which is hereby incorporated by reference in its entirety for all purposes.

BACKGROUND

In digital pathology, it is frequently important to identify relative spatial locations of multiple different biomarkers. One approach for assessing multiple biomarkers includes staining each slice of a sample with a single chromogen, but alternating which chromogen is used across slices. Thus, each slide will show a single biomarker and consecutive slides show different biomarker. To assess relative location information, a registration step may then be performed to attempt to align consecutive slides, and biomarker information from consecutive slides may then be overlaid with each other. However, the registration step can be imperfect, and biological attributes of a sample may differ across adjacent slices, such that overlaid biomarkers may present an unrealistic representation.

Multiplex brightfield immunohistochemistry (MPX IHC) imaging provides an advantage of providing images showing multiple biomarkers on a single slide. Thus, a given image can be used to simultaneously analyze the multiple biomarkers (e.g., to identify locations of biomarkers of one type relative to biomarkers of another type). For example, FIGS. 1A-1C show slides from three duplex assays where a slice was stained with two biomarkers with counterstains (Hematoxylin). FIG. 1A shows a color-corrected duplex ER/PR image from DP 200 for visualization purposes, where purple signals represent progesterone receptors (PR) and yellow signals represent estrogen receptors (ER). FIG. 1B shows a raw image generated by a scan by DP200, where purple signals represent PDL1 and yellow signals represent Pan-Cytokeratin (PanCK), which is usually used as a tumor marker. FIG. 1C shows a raw image generated by a scan by iscanHT, where purple signals represent Ki67 and yellow signals represent CD8 cells.

Further, FIGS. 1D-1F show slides from multiplex assays where a slice was stained with three biomarkers with counterstains. FIG. 1D shows a slide with ER, PR, and Her2 dyes (where the Her2 dye stains the HER2 protein). FIG. 1E shows a slide with PDL1, cMET, and EGFR dyes, where the cMET dye stains the c-MET protein and the EGFR dye stains the EGFR protein. FIG. 1F shows a slide with CD8, CD3, and BCL2 dyes, where the CD8 and CD8 dyes stain the CD3, CD8, and BCL-2 proteins, respectively.

Pathologists score biomarker expression levels by estimating from the intensity level appeared on the slides. However, using multiplexing images, it is a challenging task for pathologists to estimate the biomarker expression levels, especially, the co-localization of multiple biomarkers. Therefore, each single biomarker with counterstain images corresponding to those multiplex images are required for the pathologist scoring task. A single biomarker image may be called a singleplex image, which can be obtained by unmixing multiplex images and remixing (or reconstructing) the unmixed single biomarker with a Hematoxylin channels to become an image called synthesis singleplex.

The color unmixing can be performed as a preprocessing step to decompose multiplex brightfield images into separate color image channels. The separated color channel of a biomarker can be remixed with counterstain to generate a synthesis singleplex (simplex) image for pathologist scoring or automatic image analysis. The color unmixing can use a color-deconvolution method to decompose an RGB image into its individual-constituent chromogen for each biomarker. However, color unmixing typically is imperfect. Because standard imaging typically has three color channels (e.g., red, green and blue channels), the imperfections of color unmixing are amplified in situations where a slice is stained with more than three dyes (which may include a first dye to stain nuclei and at least three other dyes to stain three other types of biomarkers). This circumstance can lead to an infinite number of solutions for color unmixing.

FIG. 2 summarizes some of the advantages and disadvantages of the two techniques for analyzing multiple biomarkers using singleplex images. The singleplex images can be obtained: (I) Staining individual slices with multiple stains, performing color unmixing and then remixing to generate a synthesis singleplex image to detect distinct signals; and (II) Staining adjacent slices with each single stain to generate multiple actual singleplex staining images. FIG. 3 illustrates the variation factors that may influence a performance of an unmixing algorithm or registration algorithm e.g., multiple staining protocols, scanners, sites, etc.

While the first approach based on unmixing and remixing provides perfect tissue matching, reduce the tissue needed (as compared to the adjacent-slide approach), and do not require registration, unmixing parameter values must be identified. Parameter values are further specific to contexts, such that different parameter values are likely to be needed in instances where:

Different staining protocols are used;
Different tissue types are being assessed;
Different scanners are being used;
Equipment from different manufacturers are being used;
Samples are processed in different sites; and/or
Different pre-analytical conditions exist.

Unlike unmixing, the adjacent staining approach may be influenced by the performance of a registration protocol when performing the tissue analysis on multiplex images. Although the biomarker intensity on the adjacent slide is real biological staining, it is required a registration algorithm to align the tissue region with multiplex image for tissue analysis in order to locate the same tissue region for each singleplex image. However, the performance of a given registration algorithm may be good when used for a first type of tissue and poor when used for a second type of tissue. Accordingly, registration parameter values may be learned for each of multiple contexts, which is a time-consuming and expensive effort. When separate parameter values are not learned for different context, the algorithms may be un-robust and inaccurate.

SUMMARY

In some embodiments, a computer-implemented method is provided that includes accessing a multiplex image that depicts a particular slice of a particular sample stained with two or more dyes (e.g., two or more chromogens) and generating, using a Generator network, a predicted singleplex image that depicts the particular slice of the particular sample stained with only one of the two or more dyes. The Generator network may have been trained by training a machine-learning model using a set of training multiplex images and a set of training singleplex images, where each of the set of training multiplex images depicted a slice of a sample stained with two or more dyes, and where each of the set of training singleplex images depicted a slice of a sample stained with a single dye. The machine-learning model included a Discriminator network configured to discriminate as to whether a given image was generated by the Generator network or was a singleplex image of a real slide. The method further includes outputs the predicted singleplex image.

Each of the set of training singleplex images may have been a synthetic image generated by processing a corresponding training multiplex image of the set of training multiplex images using an unmixing and remixing algorithm configured for a context in which the corresponding training multiplex image was obtained.

The machine learning model may have included a Pix2Pix model or BicycleGAN.

Each of the set of training singleplex images may have been a real image depicting a corresponding slice not depicted in any of the set of training multiplex images.

The machine-learning model may have included a CycleGAN, where the CycleGAN included another Generator network configured to generate a predicted multiplex image for each received singleplex image and another Discriminator network configured to discriminate as to whether a given image was generated by the other Generator network or was a multiplex image of a real slide.

The method may further include performing, prior to generating the predicted singleplex image, the training of the machine-learning model.

The multiplex image may have generated at a first site using a first scanner, and the method may further include: accessing another multiplex image that depicts another particular slice of another particular sample stained with the two or more dyes; generating, using the Generator network, another predicted singleplex image that depicts the other particular slice stained with only one of the two or more dyes, where the Generator network was configured with same parameter values when the predicted singleplex image was generated and when the other predicted singleplex image was generated; and outputting the other predicted singleplex image.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTIONS OF THE DRAWINGS

The patent or application file contains at least one drawing executed in color. Copies of this patent or patent application publication with color drawing(s) will be provided by the Office upon request and payment of the necessary fee.

Aspects and features of the various embodiments will be more apparent by describing examples with reference to the accompanying drawings, in which:

FIGS. 1A-1F shows slides from multiplex assays where a tissue slide was stained with two dyes.

FIG. 2 summarizes some of the advantages and disadvantages of the two techniques for analyzing multiple biomarkers.

FIG. 3 illustrates contexts that may influence a performance of an unmixing algorithm or registration algorithm.

FIG. 5 exemplifies the architecture and training of a CycleGAN.

Figure 6:
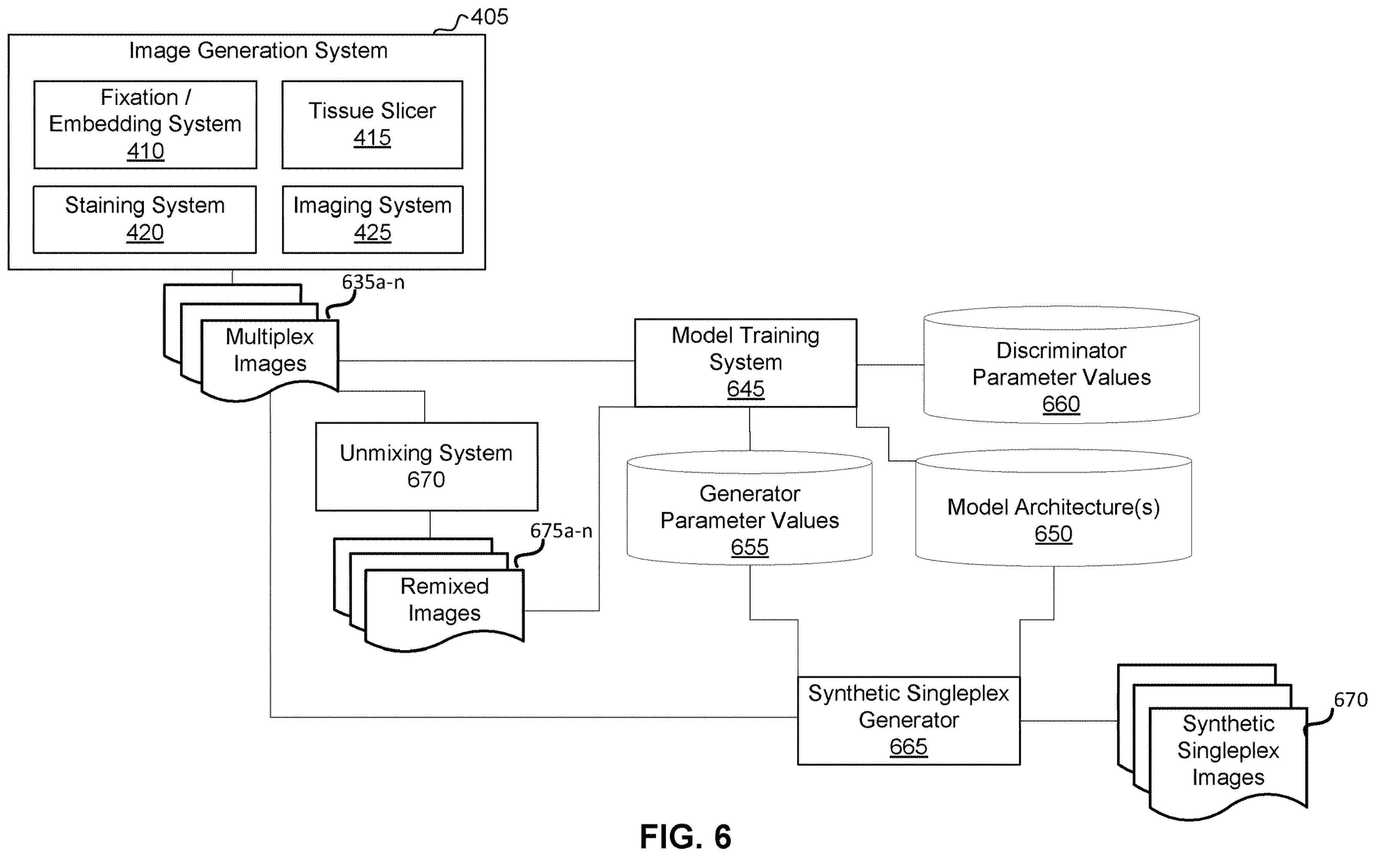

FIG. 6 shows another exemplary network for generating a synthetic singleplex image.

Figure 7:
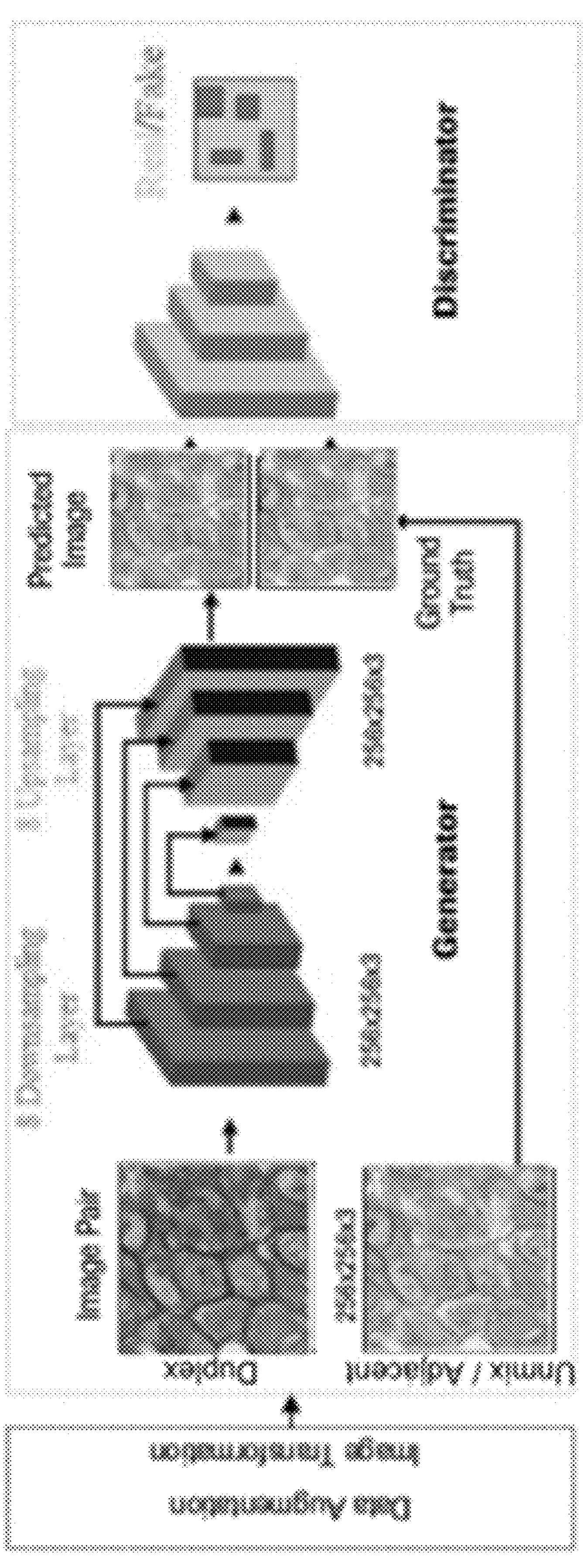

FIG. 7 illustrates an exemplary Pix2Pix GAN model that a model training system may train.

FIG. 8 shows exemplary input images, predicted singleplex images by a Generator network, and comparison singleplex images generated by an unmixing algorithm.

FIG. 9 shows additional exemplary input images, predicted singleplex images by a Generator network, and comparison singleplex images generated by an unmixing algorithm.

FIG. 10 shows additional exemplary input images, predicted singleplex images by a Generator network, and comparison singleplex images obtained by imaging adjacent slides stained with a single dye (e.g., biomarker with counterstain).

FIG. 11 shows two comparisons of input multiplex IHC images (left sides of the pair) and predicted synthetic singleplex images for each biomarker of a multiplex IHC image.

FIGS. 12A-12D show exemplary images demonstrating the performance of two techniques for generating synthetic singleplex images.

Figure 13:
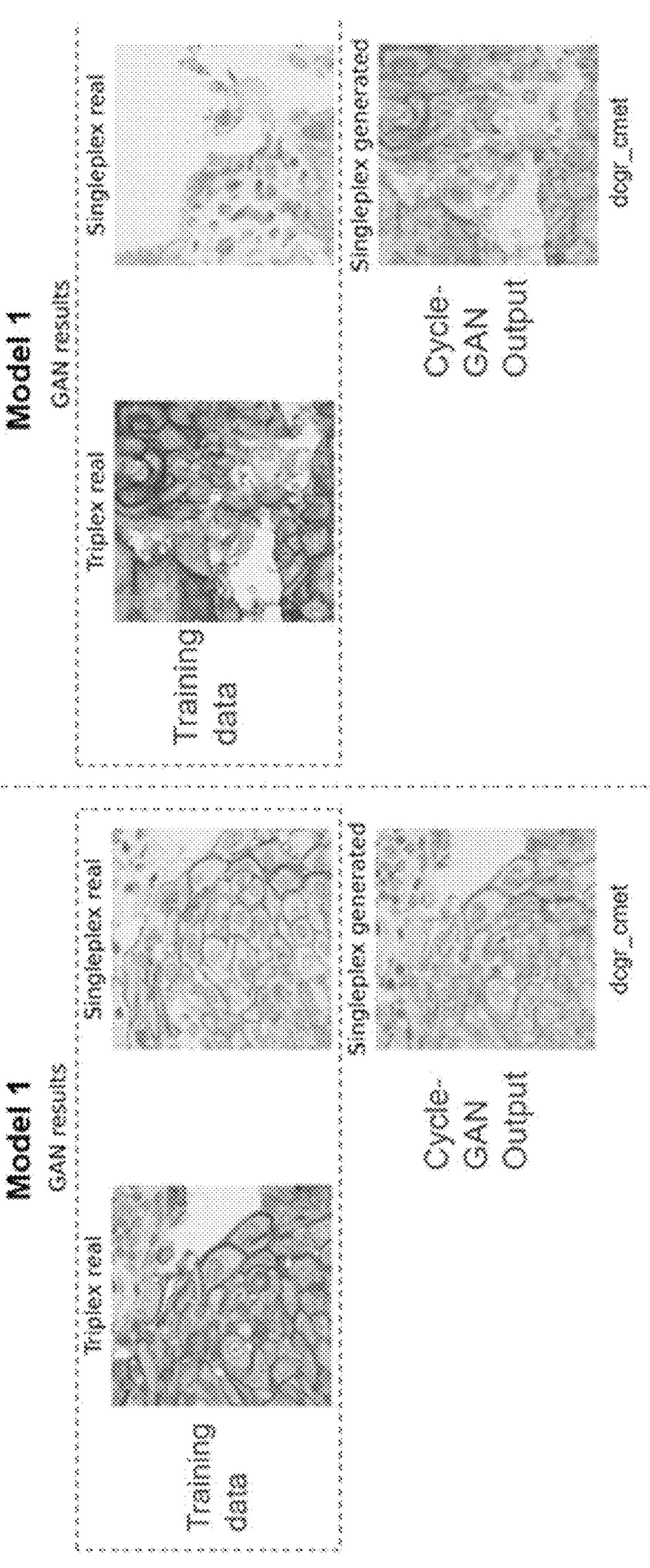
Figure 14:
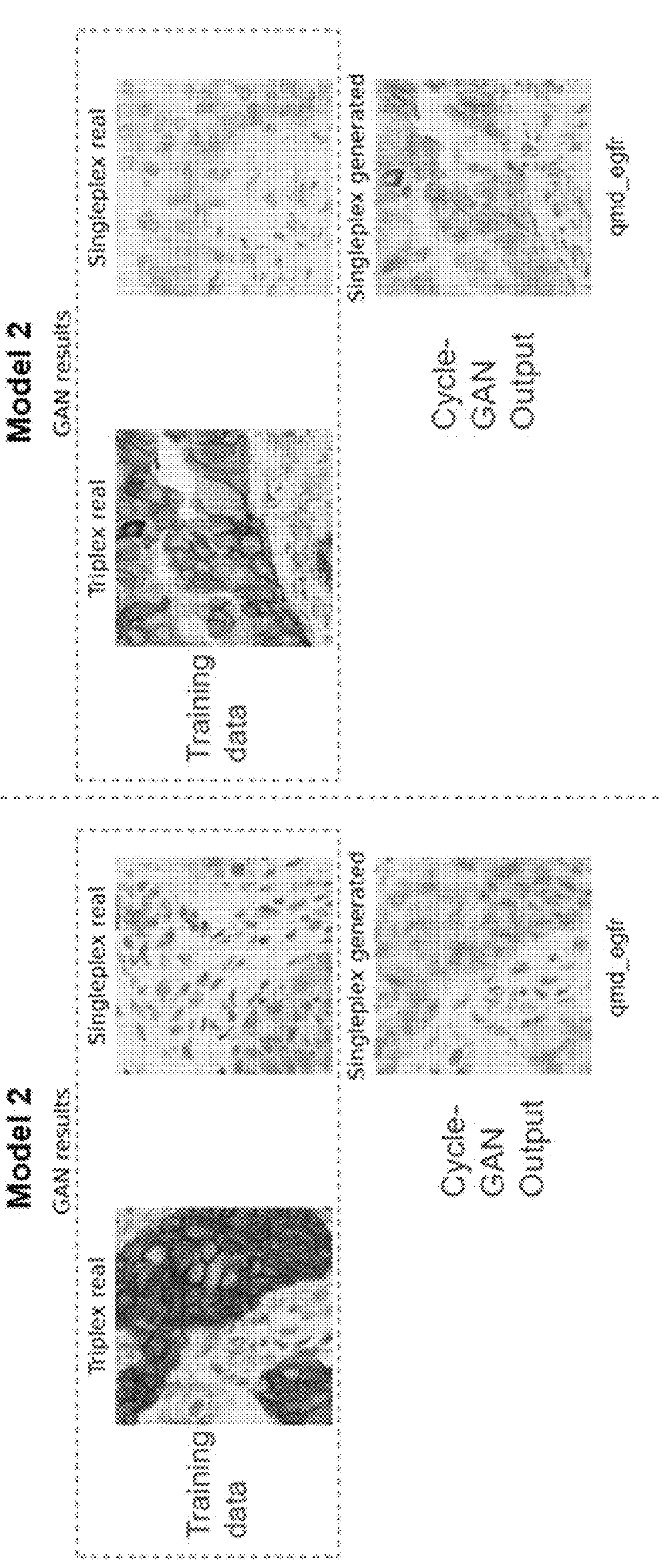
Figure 15:
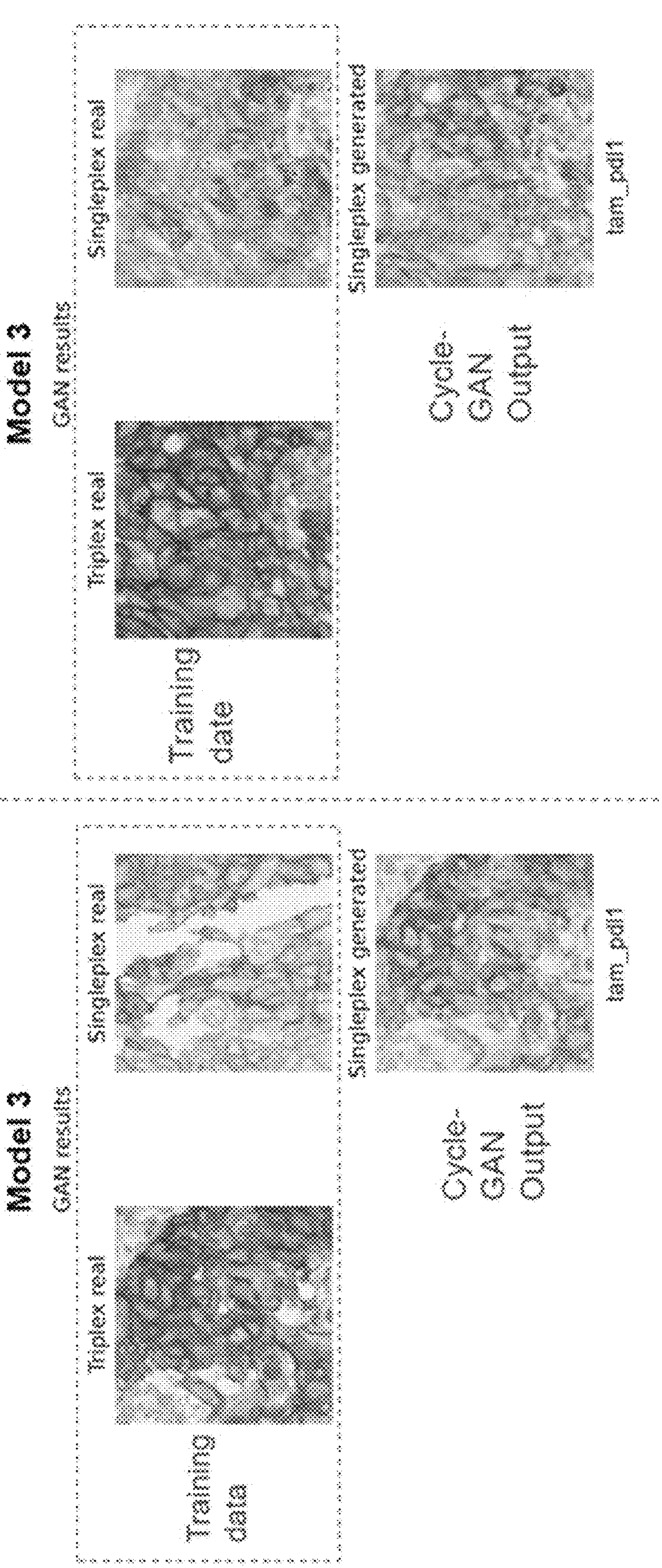

FIGS. 13-15 show exemplary images demonstrating the performance of networks trained using a CycleGAN techniques for generating synthetic singleplex images.

FIGS. 16A-16D show exemplary images demonstrating the performance of two techniques for generating synthetic singleplex images.

FIGS. 17-21 show exemplary images demonstrating the performance of networks trained using a CycleGAN techniques for generating synthetic singleplex images.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

In some embodiments, a machine-learning model is or was trained and is used to generate synthesis singleplex images from multiplex (MPX) immunohistochemistry (IHC) images. Accordingly, neither a traditional unmixing algorithm (e.g., that is based on deconvolution) nor a registration is needed to identify and assess relative spatial locations of multiple biomarkers. Whereas conventional unmixing algorithms perform poorly when applied to different protocols, tissues, subjects, cancers or sites, machine-learning models identified herein can robustly generate singleplex images across different contexts.

The machine-learning model can include a Generator that receives a real image and generates a predicted singleplex image. The real image may be a multiplex image or may be an image corresponding to a remixing image from an unmixing algorithm or an adjacent slice. The Generator may have been configured with parameter values that were learned as a result of training a larger model (e.g., that includes a Discriminator), such as a Pix2Pix model, Pix2PixHD or a GAN model (e.g., a CycleGAN model or BicycleGAN). While the Generator network may be specific to the stains that are used in an input image, it may be sufficiently general to apply (for example) across different subjects, across different protocols for applying the stains, across different tissue types, across different equipment pieces (e.g., individual scanners), across different equipment manufacturers, across different sites where slides are made, and/or across different pre-analytical conditions.

Figure 1C:
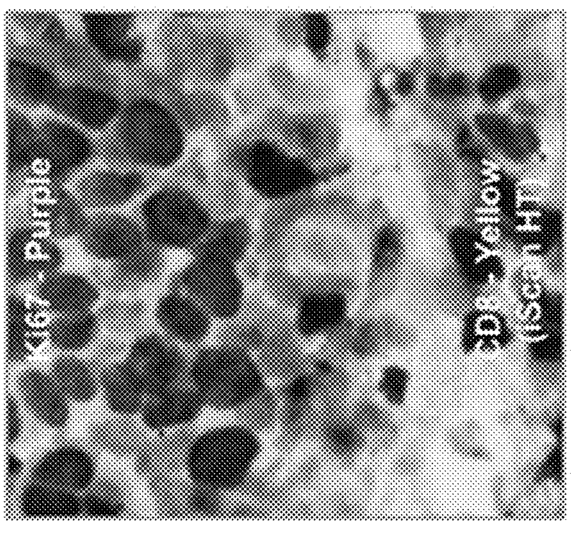
Figure 1B:
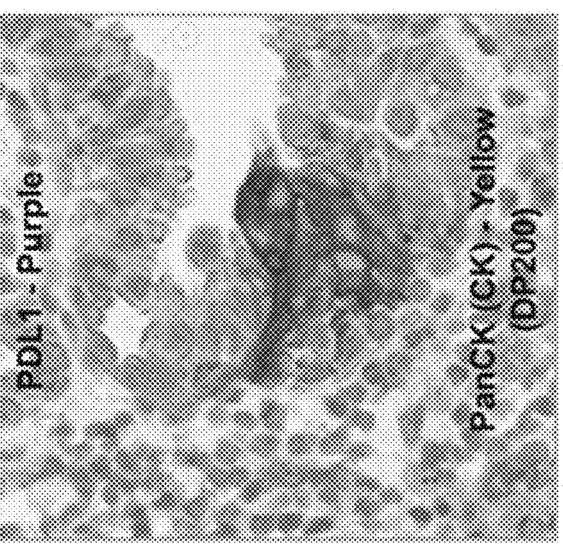
Figure 1A:
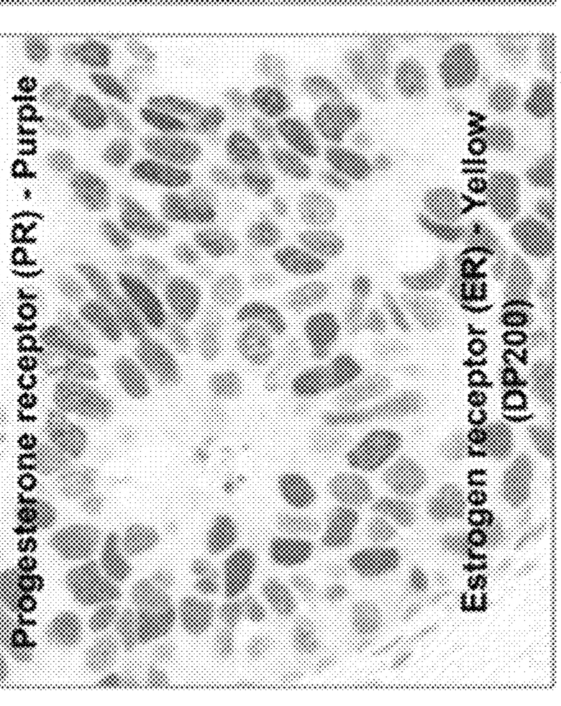
Figure 4:
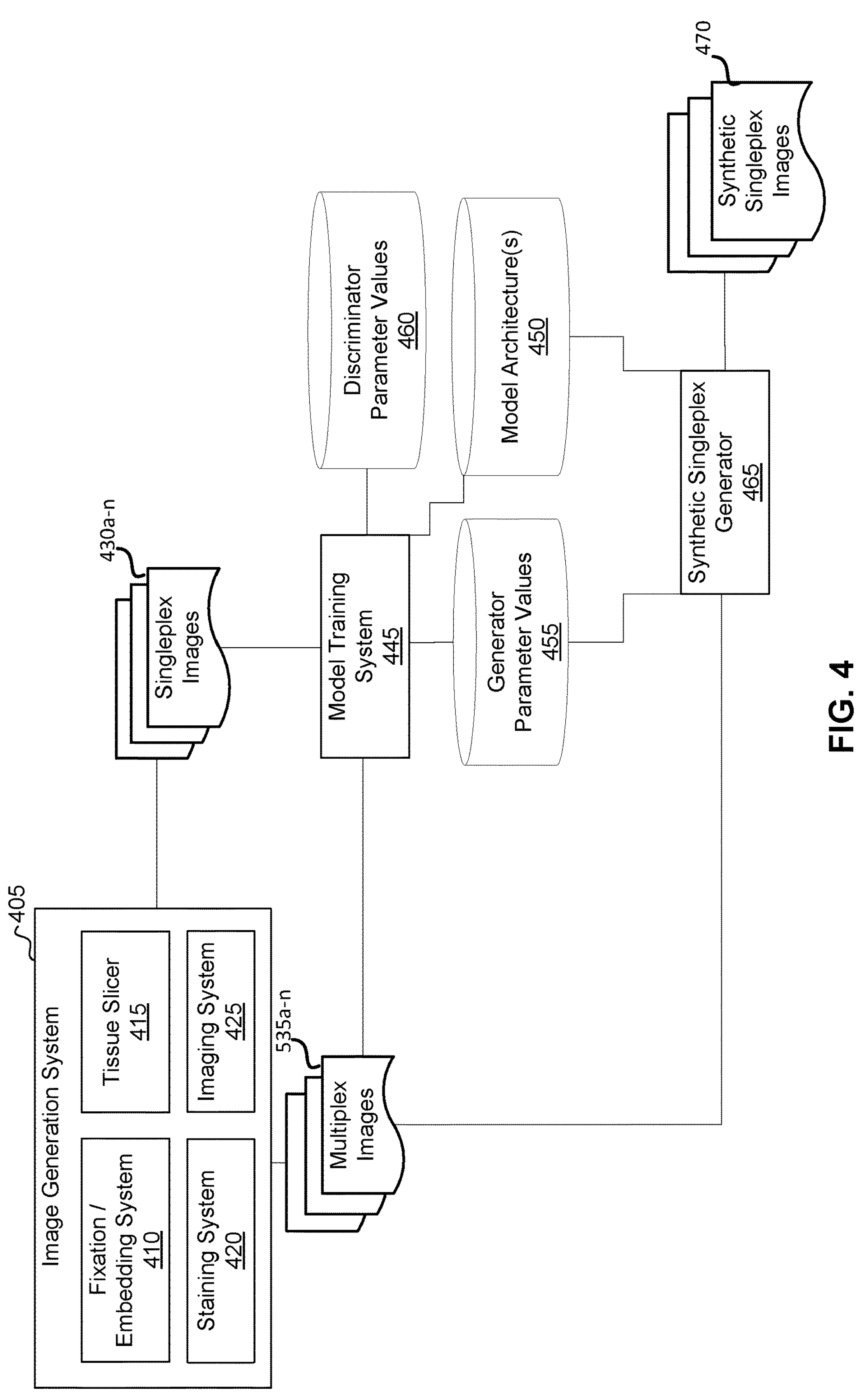
FIG. 4 shows an exemplary network for generating a synthetic singleplex image. Images are generated at an image generation system.

FIG. 4 shows an exemplary network for generating a synthetic singleplex image. Images are generated at an image generation system 405. A fixation/embedding system 410 fixes and/or embeds a tissue sample (e.g., a sample including at least part of at least one tumor) using a fixation agent (e.g., a liquid fixing agent, such as a formaldehyde solution) and/or an embedding substance (e.g., a histological wax, such as a paraffin wax and/or one or more resins, such as styrene or polyethylene). Each slice may be fixed by exposing the slice to a fixating agent for a predefined period of time (e.g., at least 3 hours) and by then dehydrating the slice (e.g., via exposure to an ethanol solution and/or a clearing intermediate agent). The embedding substance can infiltrate the slice when it is in liquid state (e.g., when heated).

A tissue slicer 415 then slices the fixed and/or embedded tissue sample (e.g., a sample of a tumor) to obtain a series of sections, with each section having a thickness of, for example, 4-5 microns. Such sectioning can be performed by first chilling the sample and the slicing the sample in a warm water bath. The tissue can be sliced using (for example) using a vibratome or compresstome.

Because the tissue sections and the cells within them are virtually transparent, preparation of the slides typically includes staining (e.g., automatically staining) the tissue sections in order to render relevant structures more visible. In some instances, the staining is performed manually. In some instances, the staining is performed semi-automatically or automatically using a staining system 420.

The staining can include exposing an individual section of the tissue to one or more different stains (e.g., consecutively or concurrently) to express different characteristics of the tissue. For example, each section may be exposed to a predefined volume of a staining agent for a predefined period of time. A duplex assay includes an approach where a slide is stained with two biomarker stains. A singleplex assay includes an approach where a slide is stained with a single biomarker stain. A multiplex assay includes an approach where a slide is stained with two or more biomarker stains. A triplex assay includes an approach where a slide is stained with three biomarker stains (e.g., with a nucleus staining biomarker). For any of the singleplex, duplex, triplex, or multiplex assays, the slide may further be stained with a stain absorbed by cell nuclei (e.g., Heme dye).

One exemplary type of tissue staining is histochemical staining, which uses one or more chemical dyes (e.g., acidic dyes, basic dyes, chromogens) to stain tissue structures. Histochemical staining may be used to indicate general aspects of tissue morphology and/or cell microanatomy (e.g., to distinguish cell nuclei from cytoplasm, to indicate lipid droplets, etc.). One example of a histochemical stain is hematoxylin and eosin (H&E). Other examples of histochemical stains include trichrome stains (e.g., Masson's Trichrome), Periodic Acid-Schiff (PAS), silver stains, and iron stains. The molecular weight of a histochemical staining reagent (e.g., dye) is typically about 500 kilodaltons (kD) or less, although some histochemical staining reagents (e.g., Alcian Blue, phosphomolybdic acid (PMA)) may have molecular weights of up to two or three thousand kD. One case of a high-molecular-weight histochemical staining reagent is alpha-amylase (about 55 kD), which may be used to indicate glycogen.

Another type of tissue staining is immunohistochemistry (IHC, also called "immunostaining"), which uses a primary antibody that binds specifically to the target antigen of interest (also called a biomarker). IHC may be direct or indirect. In direct IHC, the primary antibody is directly conjugated to a label (e.g., a chromophore or fluorophore). In indirect IHC, the primary antibody is first bound to the target antigen, and then a secondary antibody that is conjugated with a label (e.g., a chromophore or fluorophore) is bound to the primary antibody. The molecular weights of IHC reagents are much higher than those of histochemical staining reagents, as the antibodies have molecular weights of about 150 kD or more.

The sections may be then be individually mounted on corresponding slides, which an imaging system 425 can then scan or image to generate raw digital-pathology images 430*a-n*. In some instances, adjacent slides are stained with a different quantity of stains. For example, every other slide may include a sample stained with only a first particular stain or with only a second particular stain (such that singleplex images 430*a-n* are generated when the slides are imaged), and each of the remaining slides may include a sample stained with both the first particular dye and the second particular dye, such that multiplex images 435*a-n* generated when the slides are imaged are duplex images. As another example, every fourth slide from a sample may be stained with three biomarker dyes (such that a multiplex image 435*a-n* generated when the slide is imaged is a triplex image), and slides separating these three-biomarker slides may be stained with only one of the biomarker dyes (e.g., and potentially a dye absorbed by cell nuclei). It will be appreciated that, in addition to the biomarker dye(s), there may be a counterstain that is used as a location reference. For example, a counterstain may include a stain that is configured to be absorbed by cell nuclei (e.g., HTX) or cell membrane.

In some instances, rather than singleplex images 430*a-n* and multiplex images 435*a-n* corresponding to adjacent slides, they may correspond to different samples. For example, singleplex images 430*a-n* may depict slides from one or more first samples stained either only with the first particular dye or only with the second particular dye, and multiplex images 435*a-n* may depict slides from one or more second samples stained with both of the first and second particular dyes.

In either circumstance, it be appreciated that singleplex images 430*a-n* and duplex images 435*a-n* are real images that depict real slides.

A model training system 445 can use singleplex images 430*a-n* and at least some of multiplex images 435*a-n* to train a machine-learning model (e.g., that includes a convolutional machine-learning model, one or more convolutional layers, a U-Net, a V-Net, a modified U-Net, a modified V-Net, etc.). Singleplex images 430*a-n* and multiplex images 435*a-n* that are used to train the machine-learning model may, but—advantageously— need not, include paired and/or registered images.

The machine-learning model may include a Generative Adversarial Network (GAN), such as a CycleGAN or BicycleGAN. FIG. 5 exemplifies the architecture and training of a CycleGAN. The GAN can include one or more models having corresponding model architecture(s) 450. Each of the one or models can include one or more convolutional layers.

The GAN includes one or more Generator networks, including a Generator that is configured to receive one of multiplex images 435*a-n* (or a predicted duplex image) and generate a predicted singleplex image. In some instances (e.g., when the machine-learning model is a CycleGAN), the one or more Generator networks further includes a Generator that is configured to receive a one of singleplex images 430*a-n* (or a predicted singleplex image) and generate a predicted duplex image. Each of the one or more Generator networks may include (for example) a neural network, a deep neural network, a residual neural network, and/or a convolutional neural network (e.g., or a deep residual convolutional neural network, ResNet, UNET, feed forward networks).

The GAN further includes one or more Discriminator networks. Each of the one or more Discriminator networks may include (for example) a neural network, a PatchGAN, a deep neural network, and/or a convolutional neural network (e.g., a deep residual convolutional neural network). While in some instances, a Discriminator network has a same architecture as a corresponding Generator network, in other instances, the architectures are different.

A Discriminator network of the one or more Discriminator networks can be configured to predict—for a predicted singleplex image or for a singleplex image 430—whether it is a real image (e.g., generated by image generation system 405) or a predicted image. Another Discriminator network of the one or more Discriminator networks can be configured to predict—for a predicted duplex image or for a duplex image 430—whether it is a real image (e.g., generated by image generation system 405) or a predicted image. It will be appreciated that, while only one image generation system 405 is depicted, images used to train the model may be generated by multiple image generation systems 405, and/or images processed using a trained Generator network may be generated by multiple (different, overlapping, non-overlapping or same) image generation systems 405. Different image generation systems 405 may be (for example) located at different sites (e.g., at different addresses, cities, etc.).

A loss (calculated by model training system 445 and used by model training system 445 to update Generator parameter values 455 and Discriminator parameter values 460) may be calculated to depend on cycle-consistency loss, which quantifies a degree to which an original (e.g., singleplex or duplex) image differs from a corresponding image that was processed by two Generators. For example, a cycle-consistency loss may characterize the extent to which a real duplex image differs from a predicted duplex image generated by one or more first Generators transforming the real duplex image into multiple predicted singleplex images, which are then transformed by a second Generator into a predicted duplex image.

The loss may further or alternatively depend on the accuracy of predictions generated by each of the one or more Discriminator networks.

Once the GAN is trained (e.g., a loss falls below a threshold, a predefined number of training iterations are completed, etc.), a synthetic singleplex generator 465 uses the architecture and learned parameter values for the Generator configured to transform a multiplex image into one or more singleplex images to transform a non-training multiplex image 435 generated by image generation system) into a synthetic singleplex image 470. That is, after the Generator is trained (e.g., via training of a machine-learning model, such as a CycleGAN), the Generator may be separated from the machine-learning model and used independently to transform multiplex images into synthetic singleplex images.

It will be appreciated that singleplex images 430*a-n* may include images of slides stained with the same biomarker dye (and a counterstain dye, such as a counterstain dye configured to be absorbed by cell nuclei or cell membrane), and the parameter values learned during training may apply to one particular dye of multiple dyes used to stain multiplex images 435*a-n*. In this case, a different set of singleplex images may then be accessed that depict slides stained with a different biomarker dye, and model training system 445 may then train a model with model architecture(s) 450 to learn different generator parameter values and different discriminator parameter values. That is, separate training processes may be applied for each of multiple biomarker dyes depicted in multiplex images 435*a-n*, which may then result in different Generators to transform multiplex images into predicted singleplex images depicting different dyes. To illustrate, in an instance where multiplex images 435*a-n* are triplex images, there may be three different sets of singleplex images 430*a-n* (corresponding to four different biomarker dyes, including a counterstain dye), which may be used for three independent training processes to produce three different Generators.

FIG. 6 shows another exemplary network for generating a synthetic singleplex image. Elements in FIG. 6 that have reference numbers that are the same as or parallel reference numbers in FIG. 4 may include same or similar structure and may perform same or similar situation.

In the depicted instance, during a training stage, an unmixing system 670 uses a traditional unmixing algorithm to generate, for each of some multiplex images 635*a-n* (that depict slides stained with two or more or three or more stains), one or more remixed images 675*a-n*. For example, if a multiplex image depicts a slide stained with three biomarker stains, unmixing system 670 may output a single image depicting a predicted image of the slide if it were stained with one of the three biomarker stains; two images—each depicting a predicted image of the slide if it were stained with one of two of the three biomarker stains; or three images—each depicting a predicted image of the slide if it were stained with one or three of the three stains. That is, remixed images 675*a-n* may include images of predicted singleplex slides corresponding to one, more or all of the stains used to prepare a corresponding multiplex image.

Unmixing system 670 can use—for each image being processed—an algorithm that was trained specific to the context in which the image was collected. For example, the unmixing algorithm can be selected based on a type of tissue, the type(s) of stain, a site location, a piece of equipment used in a corresponding image generation system, etc.

An unmixing model may use a deconvolution technique, such as one identified in Ruifrok et al. "Quantification of histochemical staining by color deconvolution" *Anal Quant Cytol Histol* 23: 291-299, 2001, which is hereby incorporated by reference in its entirety for all purposes. An unmixing model may alternatively or additionally use a Non-negative Matrix Factorization, such as one identified in Miao et al. "Endmember Extraction from Highly Mixed Data Using Minimum Volume Constrained Non-Negative Matrix Factorization," in *IEEE Transactions on Geoscience and Remote Sensing*, vol. 45, no. 3, pp. 765-777, March 2007, doi:10.1109/TGRS.2006.888466, which is also hereby incorporated by reference in its entirety for all purposes.

A multiplex image can be paired with one or more predicted singleplex images. A model training system 645 can use the paired images to train a machine learning model (e.g., that includes a convolutional machine-learning model, one or more convolutional layers, a U-Net, a V-Net, a modified U-Net, a modified V-Net, etc.).

In some instances, the machine learning model includes a conditional adversarial network or Pix2Pix GAN model (or Pix2PixHD) and/or a model configured to perform downsampling followed by upsampling. FIG. 7 illustrates an exemplary Pix2Pix GAN model that model training system 645 may train. The conditional adversarial network or Pix2Pix GAN can include one or more models having corresponding model architecture(s) 450. Each of the one or models can include one or more convolutional layers.

The conditional adversarial network or Pix2Pix GAN includes a Generator network, including a Generator that is configured to receive one of multiplex images 635*a-n* (or a predicted duplex image) and generate a predicted singleplex image. The conditional adversarial network or Pix2Pix GAN can include a downsampling layer and upsampling layer. For example, the Generator can include a U-Net, V-Net, modified U-Net, or modified V-Net.

The machine-learning model may include one or more Generator networks and/or one or more Discriminator networks. Each Generator network may be configured and trained to receive images that include depictions of samples stained with two or more particular stains and to generate predicted images of the samples stained with only one of the two or more particular stains (while another Generator network may be configured and trained to receive images that include depictures of samples stained with the two or more particular stains and to generate predicted images of samples stained with only another of the two or more particular stain. Similarly, each Discriminator network may be trained and configured to predict whether a given image that truly depicts or is predicted (by a Generator) to depict only a particular stain is real or fake. Thus, this approach can be used to support generate synthetic singleplex images base on true triplex or N-plex input images.

The machine-learning model may be configured to be trained using paired images. Within each pair:

One image may depict a slide where a sample was stained with at least two stains or at least three stains; and Each of one or more other images include an unmixed image (that was generated for a particular context) that is predicted—using a context-specific unmixing model—to depict a single one of the at least two or at least three stains.

The Discriminator network can be configured to predict whether a given image is a fake image generated by the Generator network or a real image in the training data set. The Discriminator network can include a convolutional network and/or one or more convolutional layers.

A loss (calculated by model training system 645 and used by model training system 645 to update Generator parameter values 655 and Discriminator parameter values 660) may be calculated to depend on accuracy of predictions generated by the Discriminator network.

Once the Pix2Pix model is trained (e.g., a loss falls below a threshold, a predefined number of training iterations are completed, etc.), a synthetic singleplex generator 665 uses the architecture and learned parameter values for the Generator configured to transform a multiplex image into one or more singleplex images to transform a non-training duplex image 635 generated by image generation system) into a synthetic singleplex image 665.

It will be appreciated that variations of the disclosed embodiments are considered. For example, augmentation of the input image can be applied by perturbating the unmixed images e.g., yellow and purple channels, and then the resulting images can be remixed back to new (or augmented) duplex. The new remixed images can be used as input (source) images, and the perturbated simplex (synthesis simplex through conventional unmixing plus perturbation) can be used as a target to train a machine-learning model. In this way, variations or data augmentations can be introduced to the training data without acquiring additional real data. These variations of the training data can improve the robustness of the deep-learning models, and the GAN models can handle more variations of the input images. As a result, it may be unnecessary to generate unmixing parameters for each single dataset as ground-truth data for training a machine-learning model (e.g., a Pix2Pix model).

As another example, embodiments may be expanded to use similar training and modeling approaches to faithfully map the biomarker expression level, i.e., the intensity of the marker signal in the synthesis singleplex as the true representation of the biomarker expression, which is measured by the intensity of the unmixed images. Further, quantified metrics can be used to evaluate co-localizations and biomarker expression levels and improve the robustness of the proposed approaches.

As explained and demonstrated herein, techniques disclosed herein for training and using one or more Generator networks have multiple technical advantages. The techniques are robust to diverse circumstances and do not require particular stains, particular staining protocols, tissue types, scanners, etc., given that a model may be trained using any of a variety of image sets. Further, unlike an unmixing and remixing approach, techniques disclosed herein can also be used when dyes used to stain slices are not required pure reference colors. Additionally, models disclosed herein can be trained even when the match between singleplex and multiplex images in the training set is imperfect, poor, or even absent. Finally, techniques disclosed herein can be used to generate synthetic singleplex images even when the multiplex images depict a large number of biomarker dyes (e.g., 3 biomarker dyes, 4 biomarker dyes, 5 biomarker dyes, or more). Meanwhile, the accuracy of other existing techniques for generating synthetic singleplex images (e.g., non-negative factorization or singular value decomposition) plummets when more than two biomarker dyes are depicted in multiplex images, given that there can be thousands of combinations of singleplex signals that would result in a given multiplex image. While additional regularization may reduce the number of possible solutions, such regularization is case-specific (not generalizable across workflows, equipment, and assays) and is also insufficient to generate highly accurate predictions.

EXAMPLES

Example 1

A Pix2Pix network was trained using paired images of MPX IHC/singleplex unmixing with a combination of data from multiple assays, scanners, and cancer indications, and subjects. The following data were used to train to generate each GAN in a corresponding Pix2Pix model:

- Duplex ER/PR with 2 slides, scanned with DP200, with a total of 1,000 patches of a patch size of 128×128.
- Duplex PDL1/PanCK with 2 slides, scanned with DP200, with a total of 1,000 patches of a patch size of 128×128.
- Duplex Ki67/CD8 with 10 slides from 10 patients, scanned with iScanHT, with a total of 1,000 patches of a patch size of 128×128.

FIGS. 8 and 9 show the input image (first column); the predicted singleplex image for one stain (second column); the "true" singleplex image for the one stain as identified using a context-specific unmixing algorithm (third column); the predicted singleplex image for another stain (fourth column); and the "true" singleplex image for the other stain as identified using a context-specific unmixing algorithm (fifth column). The three rows correspond to different stains (and thus, different Generator models). As illustrated, the predicted singleplex images are realistic and very similar to the "true" singleplex images across testing images with different biomarkers, scanners, cancer indications, and subjects.

These results illustrate that—using standard unmixing approaches—it requires at least 3 different image-analysis algorithms (i.e., ER/PR, PDL1/PanCK, and Ki67/CD8) to generate those different unmixing images. However, one GAN deep-learning network (trained as part of the Pix2Pix model) with 2 models generated predicted images of very similar quality.

Example 2

A CycleGAN network was trained using unpaired images of MPX IHC/singleplex adjacent slide images from multiple assays and multiple subjects. The following data were used to train each GAN model as part of the CycleGAN network:

- Duplex ER/PR with 2 slides, scanned with DP200, with a total of 510 patches of a patch size of 128×128.
- Duplex PDL1/PanCK with 2 slides, scanned with DP200, with a total of 550 patches of a patch size of 128×128.

In FIG. 10, the first column shows exemplary input images fed to a first Generator trained as part of a CycleGAN. The second column shows a synthetic singleplex image generated by the first Generator. The third columns show true singleplex images corresponding to slides adjacent to those of the input images. Columns 4-6 show the same type of data as in columns 1-3 but corresponding to a different Generator (trained as part of a different CycleGAN to generate synthetic images corresponding to a different dye). As can be seen, the predicted images are highly similar to the synthetic images.

FIG. 11 shows two comparisons of input multiplex IHC images (left sides of the pair) and predicted synthetic singleplex images for each biomarker that may present in the input multiplex IHC image. The left images correspond to a different dye (with regard to the prediction) relative to the right images.

Thus, the output images show realistic and are comparable to the targeted unmixing images for all testing images with different biomarkers, cancer indications, and patients. The output synthesis images show matched structures as compared to the input MPX IHC images and the colors (e.g., yellow, purple) of the output images show similar to the reference adjacent slides. These results show that the unpaired image-to-image translation method works substantially to generate the matched both structures and colors of synthesis images.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification, and variation of the concepts herein disclosed may be resorted to by those skilled in the art, and that such modifications and variations are considered to be within the scope of this invention as defined by the appended claims.

The description provides preferred exemplary embodiments only, and is not intended to limit the scope, applicability or configuration of the disclosure. Rather, the description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Example 3

An assay was performed on each of multiple samples (36 total slides from 3 subjects), where the dyes used to stain the slides were PDL1 (TAMRA, membrane), cMET (Green, membrane), EGFR (Dabsyl, membrane), and Heme (nucleus). Thus, triplex slides were generated.

A CycleGAN network was trained three times independently using unpaired images of triplex IHC and singleplex adjacent slide images corresponding to one of three particular dyes for the training from multiple assays and multiple subjects. The triplex images included depictions of PDL1, cMET and EGFR dyes.

The CycleGAN network included two Generator networks (one configured to transform a triplex image into a singleplex image and the other to transform a singleplex image into a triplex image) with a deep residual convolutional neural network architecture) and two Discriminator networks (one configured to transform a singleplex image into a triplex image and the other to transform a triplex image into a singleplex image) with a PatchGAN architecture. Each of the images in the training data was of a size of 256×256 pixels and corresponded to a patch of a digital pathology slide. During training, an Adam optimizer with a learning rate of 0.0002 was used. A loss function was defined where weighting of different losses for the Generator was set to be 1, 5, and 10 for the adversarial, identity and cycle consistency, respectively. A batch size of 8 was used.

With respect to each of the three dyes, after the CycleGAN network was trained, the Generator configured to generate synthetic singleplex images were then used to process another triplex image to generate a synthetic singleplex image corresponding to the dye. FIGS. 12A and 12B show an exemplary triplex image and a synthetic singleplex image for the green dye produced by the Generator. The bottom portion of FIG. 12B further shows enlarged portions of the synthetic singleplex image.

A real synthetic singleplex image from an adjacent slide was accessed for comparative purposes. (See FIG. 12C.)

Additionally, non-negative factorization (NMF) with additional regularization was used to generate a comparative synthetic singleplex image for the dye. (See FIG. 12D.)

The arrows pointed in the southwest direction point towards membrane stains. The arrows pointed in the northwest direction point towards nucleus stains.

It can be seen that the stain level of the synthetic singleplex generated by the Generator that was trained as part of the CycleGAN corresponds to the level in the real adjacent slide better than synthetic singleplex generated by the NMF technique. The stain level of the synthetic singleplex generated by the NMF technique is lower than what is present in real slides.

Additionally, the synthetic singleplex image generated by the Generator that was trained as part of the CycleGAN reliably depicts nuclei. Meanwhile, due to the customization required for the NMF technique to reduce stain decomposition errors, nucleus stains are separated first from the triplex (to reduce the number of stains to three in the image and thus uniqueness of the stain decomposition results by NMF and then added back to the synthetic singleplex, which led to partly missing nucleus signals. (Consider the missing northwest-pointing arrow in FIG. 12D.)

Further, in the synthetic singleplex image generated by the Generator that was trained as part of the CycleGAN, the membrane stains are sharp and correspond to those in the triplex image. However, in the synthetic singleplex generated by the NMF technique, the membrane stains are less sharp and have a weaker correspondence to those in the triplex image.

FIG. 13 shows another illustrative example of a synthetic singleplex Green-cMET image generated by transforming a triplex PDL1-cMET-EGFR image using the Generator that was trained as part of the CycleGAN network. FIG. 14 shows another illustrative example of a synthetic singleplex QM-Dabsyl-EGFR image generated by transforming a triplex PDL1-cMET-EGFR image using the Generator that was trained as part of the CycleGAN. FIG. 15 shows another illustrative example of a synthetic singleplex Tamra-PDL1 image generated by transforming a triplex PDL1-cMET-EGFR image using the Generator that was trained as part of the CycleGAN. Each of FIGS. 13-15 further shows exemplary real triplex and singleplex images used for testing the network. It can be seen that the color intensity, sharpness, and texture of the synthetic singleplex images generated using a Generator that was trained as part of a Cycle GAN are highly similar to those in the corresponding images.

Example 4

An assay was performed on each of multiple samples (36 total slides from 3 subjects), where the dyes used to stain the slides were CD8 (TAMRA, membrane), Bcl2 (Green, membrane), CD3 (Dabsyl, membrane), and Heme (nucleus). Thus, triplex slides were generated.

A CycleGAN network was trained three times independently using unpaired images of triplex IHC and singleplex adjacent slide images corresponding to one of three particular dyes for the training from multiple assays and multiple subjects. The triplex images included depictions of CD8, Bcl2, and CD3 dyes.

The CycleGAN network included two Generator networks (one configured to transform a triplex image into a singleplex image and the other to transform a singleplex image into a triplex image) with a deep residual convolutional neural network architecture) and two Discriminator networks (one configured to transform a singleplex image into a triplex image and the other to transform a triplex image into a singleplex image) with a PatchGAN architecture. Each of the images in the training data was of a size of 256×256 pixels and corresponded to a patch of a digital pathology slide. During training, an Adam optimizer with a learning rate of 0.0002 was used. A loss function was defined where weighting of different losses for the Generator was set to be 1, 5, and 10 for the adversarial, identity and cycle consistency, respectively. A batch size of 8 was used.

With respect to each of the three dyes, after the CycleGAN network was trained, the Generator configured to generate synthetic singleplex images were then used to process another triplex image to generate a synthetic singleplex image corresponding to the dye.

FIGS. 16A and 16B show an exemplary triplex image and a synthetic singleplex image for the green dye produced by the Generator.

A real synthetic singleplex image from an adjacent slide was accessed for comparative purposes. (See FIG. 16C.)

Additionally, non-negative factorization (NMF) with additional regularization was used to generate a comparative synthetic singleplex image for the dye. (See FIG. 16D.)

It can be seen that the stain level of the synthetic singleplex generated by the Generator that was trained as part of the CycleGAN corresponds to the level in the real adjacent slide better than synthetic singleplex generated by the NMF technique. The stain level of the synthetic singleplex generated by the NMF technique is lower than what is present in real slides. Further, the membranes in the synthetic singleplex generated by the Generator that was trained as part of the CycleGAN are sharper than those in the synthetic singleplex generated by the NMF technique.

Figure 17:
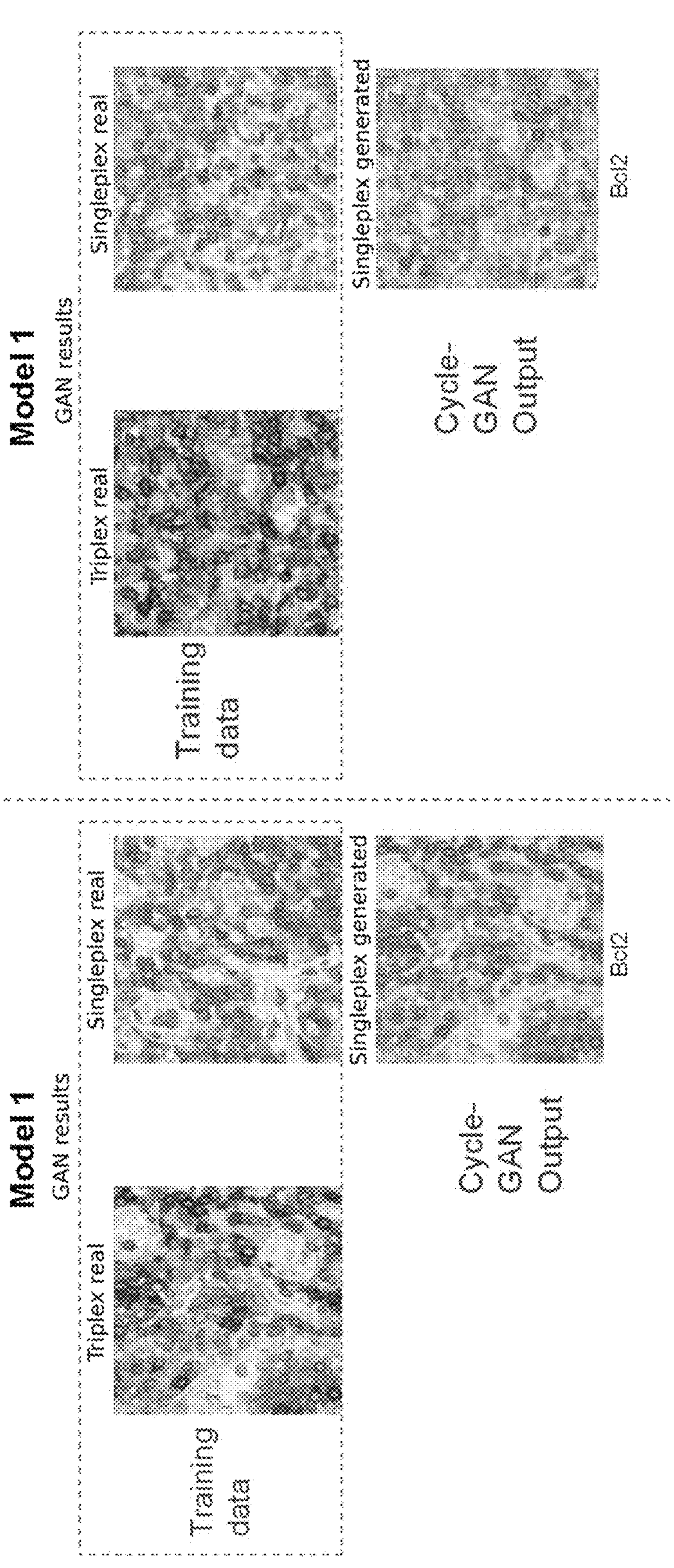
Figure 18:
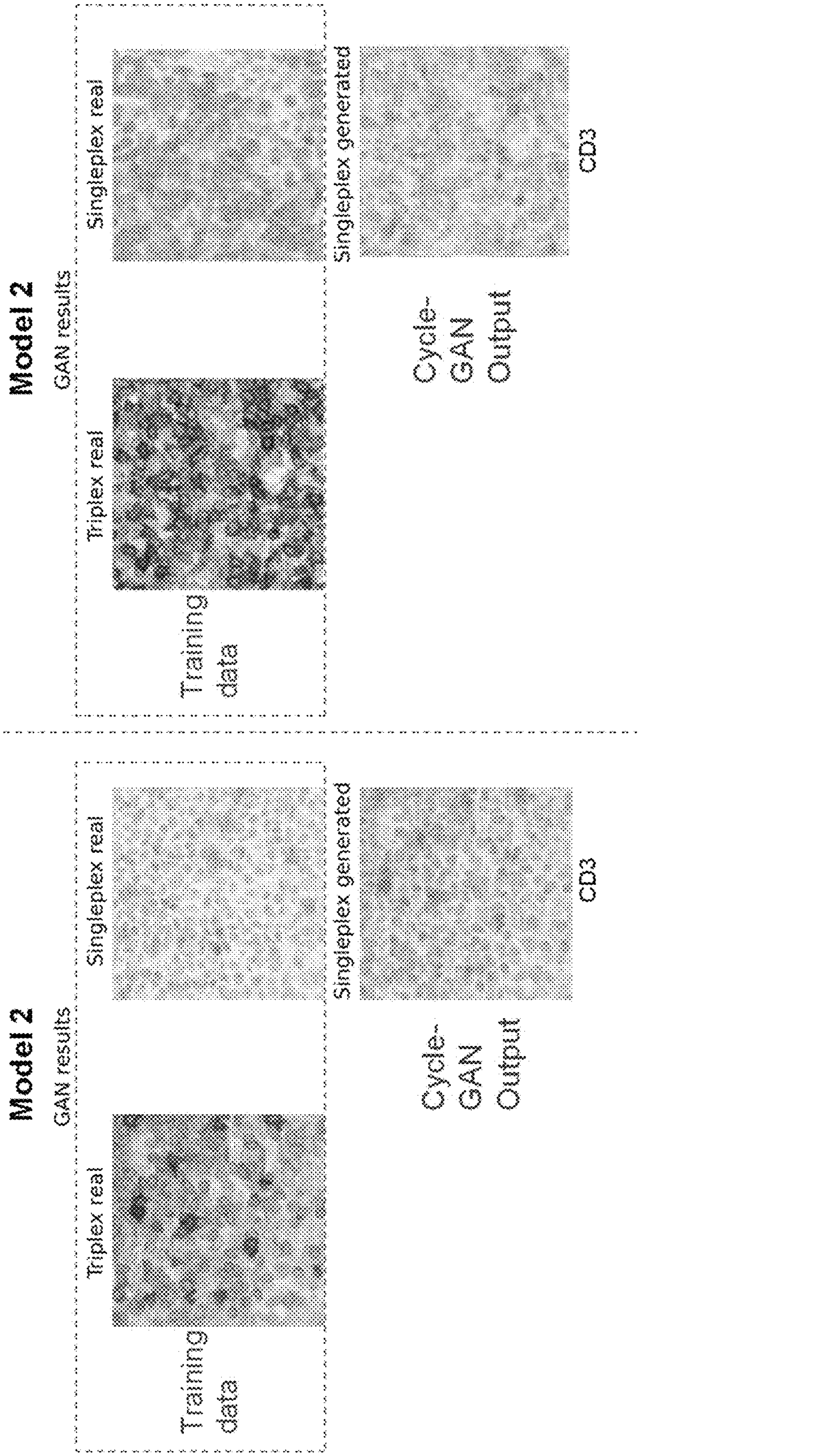
Figure 19:
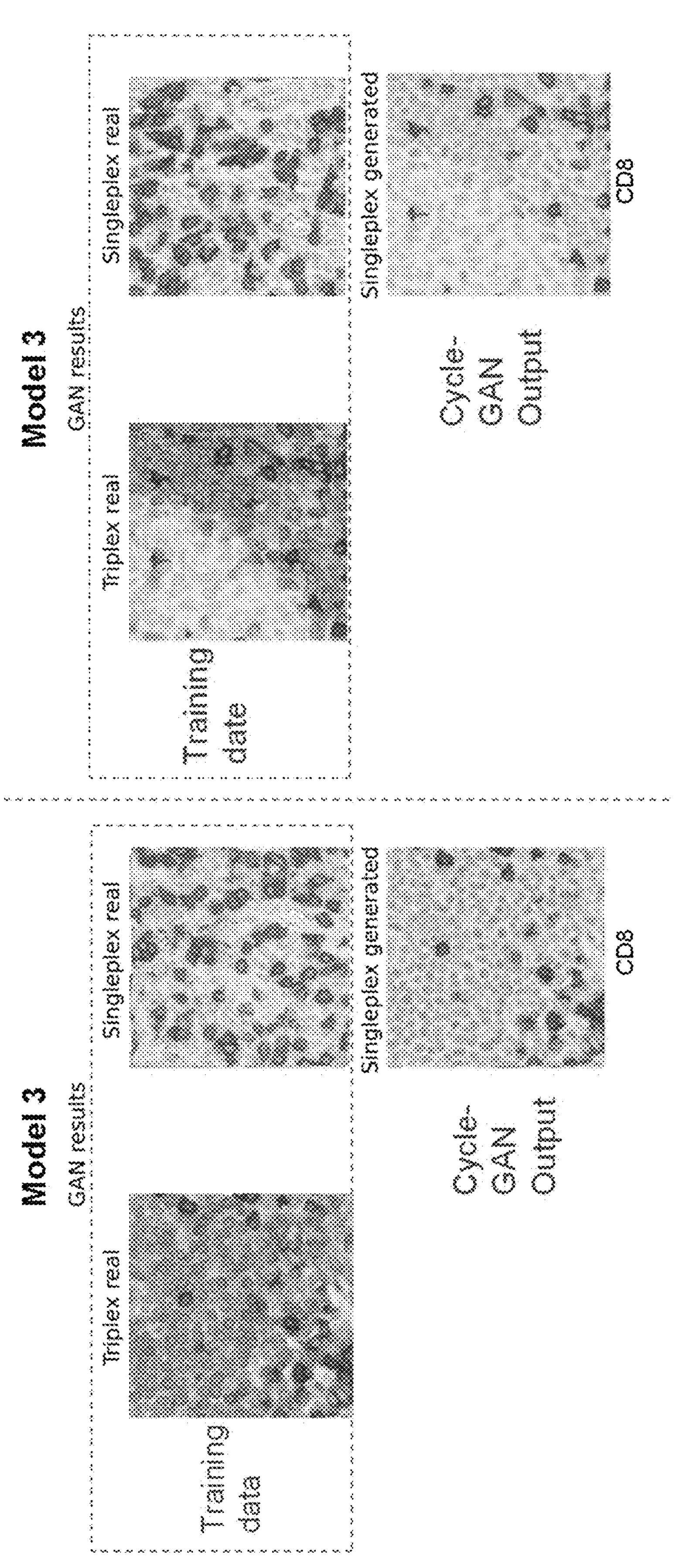

FIG. 17 shows another illustrative example of a synthetic singleplex Green-Bcl2 image generated by transforming a triplex CD8-Bcl2-CD3 image using a Generator that was trained as part of a CycleGAN). FIG. 18 shows another illustrative example of a synthetic singleplex Dabsyl-CD3 image generated by transforming a triplex CD8-Bcl2-CD3 image using a Generator that was trained as part of a CycleGAN FIG. 19 shows another illustrative example of a synthetic singleplex Tamra-CD8 image generated by transforming a triplex CD8-Bcl2-CD3 image using the Generator that was trained as part of a CycleGAN. Each of FIGS. 17-19 further shows exemplary real triplex and singleplex images used for testing the network. It can be seen that the color intensity, sharpness, and texture of the synthetic singleplex images generated using Generators that were trained as part of CycleGANs are highly similar to those in the corresponding images.

Example 5

An assay was performed on each of multiple samples, where the dyes used to stain the slides were PR (TAMRA), Her2 (Green), ER (Dabsyl), and Heme (nucleus). Thus, triplex slides were generated.

A CycleGAN network was trained three times independently using unpaired images of triplex IHC and singleplex adjacent slide images corresponding to one of three particular dyes for the training from multiple assays and multiple subjects. The triplex images included depictions of PR, Her2, and ER dyes.

The CycleGAN network included two Generator networks (one configured to transform a triplex image into a singleplex image and the other to transform a singleplex image into a triplex image) with a deep residual convolutional neural network architecture) and two Discriminator networks (one configured to transform a singleplex image into a triplex image and the other to transform a triplex image into a singleplex image) with a PatchGAN architecture.

With respect to each of the three dyes, after the CycleGAN network was trained, the Generator configured to generate synthetic singleplex images were then used to process another triplex image to generate a synthetic singleplex image corresponding to the dye.

FIG. 20 shows another illustrative example of a triplex image, a synthetic singleplex Green-Her2 image generated by transforming a triplex ER-PR-Her2 image using a Generator that was trained as part of the CycleGAN, and an adjacent slice stained with the Her2 dye, respectively.

FIG. 21 shows another illustrative example of a triplex image, a synthetic singleplex Tamra-PR image generated by transforming a triplex ER-PR-Her2 image using a Generator that was trained as part of the CycleGAN, and an adjacent slice stained with the PR dye.

It can be seen that the color intensity, sharpness, and texture of the synthetic singleplex images is highly similar to that in the corresponding images.

The invention claimed is:

1. A computer-implemented method comprising:

accessing a multiplex image that depicts a particular slice of a particular sample stained with two or more dyes;

generating, using a Generator network, a predicted singleplex image that depicts the particular slice of the particular sample stained with only one of the two or more dyes, wherein:

the Generator network was trained by training a machine-learning model using a set of training multiplex images and a set of training singleplex images, wherein each of the set of training multiplex images depicted a slice of a sample stained with two or more dyes, and wherein each of the set of training singleplex images depicted a slice of a sample stained with a single dye, and wherein one of the set of training multiplex images comprises an unmixed image associated with a type of stain to represent the particular sample stained with only one of the dyes, the unmixed image is:

decomposed from the multiplex image using a color deconvolution algorithm selected based on a context, in which the multiplex image was obtained, and perturbated to generate remixed image for the context; and the machine-learning model, trained on the remixed image, included a Discriminator network configured to discriminate as to whether a given image was generated by the Generator network or was a singleplex image of a real slide; and outputting the predicted singleplex image.

2. The computer-implemented method of claim 1, wherein each of the set of training singleplex images was a synthetic image generated by processing a corresponding training multiplex image of the set of training multiplex images using an unmixing or remixing algorithm configured for a context in which the corresponding training multiplex image was obtained.

3. The computer-implemented method of claim 1, wherein the machine-learning model included a Pix2Pix model.

4. The computer-implemented method of claim 1, wherein each of the set of training singleplex images was a real image depicting a corresponding slice not depicted in any of the set of training multiplex images.

5. The computer-implemented method of claim 1, wherein the machine-learning model included a CycleGAN or BicycleGAN, wherein the CycleGAN or BicycleGAN included:

another Generator network configured to generate a predicted multiplex image for each received singleplex image; and another Discriminator network configured to discriminate as to whether a given image was generated by the other Generator network or was a multiplex image of a real slide.

6. The computer-implemented method of claim 1, further comprising, prior to generating the predicted singleplex image, performing the training of the machine-learning model.

7. The computer-implemented method of claim 1, wherein the multiplex image was generated at a first site using a first scanner, and wherein the method further comprises:

accessing another multiplex image that depicts another particular slice of another particular sample stained with the two or more dyes;

generating, using the Generator network, another predicted singleplex image that depicts the other particular slice stained with only one of the two or more dyes, wherein the Generator network was configured with same parameter values when the predicted singleplex image was generated and when the other predicted singleplex image was generated; and outputting the other predicted singleplex image.

8. A system comprising:

one or more data processors; and a non-transitory computer readable storage medium containing instructions which, when executed on the one or more data processors, cause the one or more data processors to perform a set of actions including:

accessing a multiplex image that depicts a particular slice of a particular sample stained with two or more dyes;

generating, using a Generator network, a predicted singleplex image that depicts the particular slice of the particular sample stained with only one of the two or more dyes, wherein:

the Generator network was trained by training a machine-learning model using a set of training multiplex images and a set of training singleplex images, wherein each of the set of training multiplex images depicted a slice of a sample stained with two or more dyes, and wherein each of the set of training singleplex images depicted a slice of a sample stained with a single dye, and wherein one of the set of training multiplex images comprises an unmixed image associated with a type of stain to represent the particular sample stained with only one of the dyes, the unmixed image is:

decomposed from the multiplex image using a color deconvolution algorithm selected based on a context, in which the multiplex image was obtained, and perturbated to generate a remixed image for the context; and the machine-learning model, trained on the remixed image, included a Discriminator network configured to discriminate as to whether a given image was generated by the Generator network or was a singleplex image of a real slide; and outputting the predicted singleplex image.

9. The system of claim 8, wherein each of the set of training singleplex images was a synthetic image generated by processing a corresponding training multiplex image of the set of training multiplex images using an unmixing or remixing algorithm configured for a context in which the corresponding training multiplex image was obtained.

10. The system of claim 8, wherein the machine-learning model included a Pix2Pix model.

11. The system of claim 8, wherein each of the set of training singleplex images was a real image depicting a corresponding slice not depicted in any of the set of training multiplex images.

12. The system of claim 8, wherein the machine-learning model included a CycleGAN or BicycleGAN, wherein the CycleGAN or BicycleGAN included:

another Generator network configured to generate a predicted multiplex image for each received singleplex image; and another Discriminator network configured to discriminate as to whether a given image was generated by the other Generator network or was a multiplex image of a real slide.

13. The system of claim 8, wherein the set of actions further includes, prior to generating the predicted singleplex image, performing the training of the machine-learning model.

14. The system of claim 8, wherein the multiplex image was generated at a first site using a first scanner, and wherein the set of actions further includes:

accessing another multiplex image that depicts another particular slice of another particular sample stained with the two or more dyes;

generating, using the Generator network, another predicted singleplex image that depicts the other particular slice stained with only one of the two or more dyes, wherein the Generator network was configured with same parameter values when the predicted singleplex image was generated and when the other predicted singleplex image was generated; and outputting the other predicted singleplex image.

15. A computer-program product tangibly embodied in a non-transitory machine-readable storage medium, including instructions configured to cause one or more data processors to perform a set of actions including:

accessing a multiplex image that depicts a particular slice of a particular sample stained with two or more dyes;

generating, using a Generator network, a predicted singleplex image that depicts the particular slice of the particular sample stained with only one of the two or more dyes, wherein:

the Generator network was trained by training a machine-learning model using a set of training multiplex images and a set of training singleplex images, wherein each of the set of training multiplex images depicted a slice of a sample stained with two or more dyes, and wherein each of the set of training singleplex images depicted a slice of a sample stained with a single dye, and wherein one of the set of training multiplex images comprises an unmixed image associated with a type of stain to represent the particular sample stained with only one of the dyes, the unmixed image is:

decomposed from the multiplex image using a color deconvolution algorithm selected based on a context, in which the multiplex image was obtained, and perturbated to generate a remixed image for the context; and the machine-learning model, trained on the remixed image included a Discriminator network configured to discriminate as to whether a given image was generated by the Generator network or was a singleplex image of a real slide; and outputting the predicted singleplex image.

16. The computer-program product of claim 15, wherein each of the set of training singleplex images was a synthetic image generated by processing a corresponding training multiplex image of the set of training multiplex images using an unmixing or remixing algorithm configured for a context in which the corresponding training multiplex image was obtained.

17. The computer-program product of claim 15, wherein the machine-learning model included a Pix2Pix model.

18. The computer-program product of claim 15, wherein each of the set of training singleplex images was a real image depicting a corresponding slice not depicted in any of the set of training multiplex images.

19. The computer-program product of claim 15, wherein the machine-learning model included a CycleGAN or BicycleGAN, wherein the CycleGAN or BicycleGAN included:

another Generator network configured to generate a predicted multiplex image for each received singleplex image; and another Discriminator network configured to discriminate as to whether a given image was generated by the other Generator network or was a multiplex image of a real slide.

20. The computer-program product of claim 15, wherein the set of actions further includes, prior to generating the predicted singleplex image, performing the training of the machine-learning model.

21. The computer-program product of claim 15, wherein the multiplex image was generated at a first site using a first scanner, and wherein the set of actions further includes:

accessing another multiplex image that depicts another particular slice of another particular sample stained with the two or more dyes;

generating, using the Generator network, another predicted singleplex image that depicts the other particular slice stained with only one of the two or more dyes, wherein the Generator network was configured with same parameter values when the predicted singleplex image was generated and when the other predicted singleplex image was generated; and outputting the other predicted singleplex image.

* * * * *